(12) United States Patent
Ben Shalom

(10) Patent No.: US 12,427,091 B2
(45) Date of Patent: Sep. 30, 2025

(54) LIQUID TRANSFER DEVICES FOR USE WITH INTRAVENOUS (IV) BOTTLES

(71) Applicant: West Pharma. Services, IL, Ltd., Ra'anana (IL)

(72) Inventor: Niv Ben Shalom, Netanya (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 17/423,857

(22) PCT Filed: Jan. 7, 2020

(86) PCT No.: PCT/IL2020/050020
§ 371 (c)(1),
(2) Date: Jul. 17, 2021

(87) PCT Pub. No.: WO2020/148748
PCT Pub. Date: Jul. 23, 2020

(65) Prior Publication Data
US 2022/0040042 A1 Feb. 10, 2022

Related U.S. Application Data

(60) Provisional application No. 62/794,019, filed on Jan. 18, 2019.

(51) Int. Cl.
*A61J 1/20* (2006.01)
*A61J 1/14* (2023.01)

(52) U.S. Cl.
CPC .......... *A61J 1/2089* (2013.01); *A61J 1/1406* (2013.01); *A61J 1/1412* (2013.01); *A61J 1/1481* (2015.05);
(Continued)

(58) Field of Classification Search
CPC ...... A61J 1/2089; A61J 1/1406; A61J 1/1412; A61J 1/1481; A61J 1/201; A61J 1/2058; A61J 1/2072; A61J 1/2096
See application file for complete search history.

(56) References Cited

U.S. PATENT DOCUMENTS 62,333 A 2/1867 Hall
247,975 A 10/1881 Wickes
(Continued)

FOREIGN PATENT DOCUMENTS

CA 2946559 A1 10/2015
CN 1636605 A 7/2005
(Continued)

OTHER PUBLICATIONS

Office Action dated Jun. 15, 2011 in JP Application No. 2008-538492.
(Continued)

*Primary Examiner* — Ariana Zimbouski
(74) *Attorney, Agent, or Firm* — Blank Rome LLP

(57) ABSTRACT

A liquid transfer device is provided having a trifurcated body that includes a vial adapter at a first end configured to telescopically mount on the crown of an IV bottle to puncture a stopper in the crown with a cannula, an IV port extending from an opposing second end of the trifurcated body, and a needleless self-sealing port extending from a third end of the trifurcated body and configured to couple with the male connector of an additive transfer device. Methods of using the liquid transfer device with an IV bottle, additive transfer device, and an infusion set to prepare an infusion liquid for administration to a patient are also provided.

21 Claims, 5 Drawing Sheets

(52) U.S. Cl.
CPC .............. *A61J 1/201* (2015.05); *A61J 1/2058* (2015.05); *A61J 1/2072* (2015.05); *A61J 1/2096* (2013.01)

(56) References Cited

U.S. PATENT DOCUMENTS

| | | |
|---|---|---|
| 254,444 A | 2/1882 | Vogel et al. |
| 300,060 A | 6/1884 | Ford |
| 1,021,681 A | 3/1912 | Jennings |
| 1,704,817 A | 3/1929 | Ayers |
| 1,930,944 A | 10/1933 | Schmitz, Jr. |
| 2,326,490 A | 8/1943 | Perelson |
| 2,560,162 A | 7/1951 | Ferguson |
| 2,748,769 A | 6/1956 | Jennie |
| 2,804,224 A * | 8/1957 | Barton .................. A61J 1/1406 215/247 |
| 2,830,587 A | 4/1958 | James |
| 2,931,668 A | 4/1960 | Baley |
| 2,968,497 A | 1/1961 | Mervyn |
| 3,059,643 A | 10/1962 | Barton |
| D198,499 S | 6/1964 | Andrew et al. |
| 3,225,763 A | 12/1965 | Waterman |
| 3,277,893 A | 10/1966 | Clark |
| 3,308,822 A | 3/1967 | De Luca |
| 3,484,849 A | 12/1969 | Huebner et al. |
| 3,618,637 A | 11/1971 | Santomieri |
| 3,757,981 A | 9/1973 | Harris, Sr. et al. |
| D229,518 S | 12/1973 | Bujan |
| 3,782,365 A | 1/1974 | Pinna |
| 3,788,524 A | 1/1974 | Davis et al. |
| 3,822,700 A | 7/1974 | Pennington |
| 3,826,261 A | 7/1974 | Killinger |
| 3,872,992 A | 3/1975 | Larson |
| 3,885,607 A | 5/1975 | Peltier |
| 3,938,520 A | 2/1976 | Scislowicz et al. |
| 3,957,052 A | 5/1976 | Topham |
| 3,977,555 A | 8/1976 | Larson |
| 3,993,063 A | 11/1976 | Larrabee |
| 4,020,839 A | 5/1977 | Klapp |
| 4,026,128 A | 5/1977 | Blanco |
| 4,051,852 A | 10/1977 | Villari |
| D247,975 S | 5/1978 | Luther |
| D248,568 S | 7/1978 | Ismach |
| 4,109,670 A | 8/1978 | Slagel |
| 4,121,585 A | 10/1978 | Becker, Jr. |
| 4,161,178 A | 7/1979 | Genese |
| 4,187,848 A | 2/1980 | Taylor |
| D254,444 S | 3/1980 | Levine |
| 4,203,067 A | 5/1980 | Bollongino et al. |
| 4,203,443 A | 5/1980 | Genese |
| 4,210,173 A | 7/1980 | Choksi et al. |
| D257,286 S | 10/1980 | Folkman |
| 4,253,501 A | 3/1981 | Ogle |
| 4,262,671 A | 4/1981 | Kersten |
| 4,296,786 A | 10/1981 | Brignola |
| 4,303,067 A | 12/1981 | Connolly et al. |
| 4,312,349 A | 1/1982 | Cohen |
| 4,314,586 A | 2/1982 | Folkman |
| 4,328,802 A | 5/1982 | Curley et al. |
| 4,335,717 A | 6/1982 | Bujan et al. |
| D267,199 S | 12/1982 | Koenig |
| 4,364,387 A | 12/1982 | Larkin |
| 4,376,634 A | 3/1983 | Prior et al. |
| D268,871 S | 5/1983 | Benham et al. |
| 4,392,850 A | 7/1983 | Elias et al. |
| D270,282 S | 8/1983 | Gross |
| 4,410,321 A | 10/1983 | Pearson et al. |
| 4,411,662 A | 10/1983 | Pearson |
| D271,421 S | 11/1983 | Fetterman |
| 4,434,823 A | 3/1984 | Hudspith |
| 4,465,471 A | 8/1984 | Harris et al. |
| 4,475,915 A | 10/1984 | Sloane |
| 4,493,348 A | 1/1985 | Lemmons |
| 4,505,709 A | 3/1985 | Froning et al. |
| 4,507,113 A | 3/1985 | Dunlap |
| D280,018 S | 8/1985 | Scott |
| 4,532,969 A | 8/1985 | Kwaan |
| 4,534,758 A | 8/1985 | Akers et al. |
| 4,561,445 A | 12/1985 | Berke et al. |
| 4,564,054 A | 1/1986 | Gustavsson |
| 4,573,993 A | 3/1986 | Hoag et al. |
| 4,576,211 A | 3/1986 | Valentini et al. |
| 4,581,014 A | 4/1986 | Millerd et al. |
| 4,585,446 A | 4/1986 | Kempf |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,675,020 A | 6/1987 | Mcphee |
| 4,676,530 A | 6/1987 | Nordgren et al. |
| D291,490 S | 8/1987 | Raines |
| 4,683,975 A | 8/1987 | Booth et al. |
| 4,697,622 A | 10/1987 | Swift et al. |
| 4,721,133 A | 1/1988 | Sundblom |
| 4,729,401 A | 3/1988 | Raines |
| 4,735,608 A | 4/1988 | Sardam |
| 4,743,229 A | 5/1988 | Chu |
| 4,743,243 A | 5/1988 | Vaillancourt |
| 4,752,292 A | 6/1988 | Lopez et al. |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,797,898 A | 1/1989 | Martinez |
| D300,060 S | 2/1989 | Molgaard-Nielsen |
| 4,804,366 A | 2/1989 | Zdeb et al. |
| 4,826,492 A | 5/1989 | Magasi |
| 4,832,690 A | 5/1989 | Kuu |
| 4,834,152 A | 5/1989 | Howson et al. |
| 4,834,744 A | 5/1989 | Ritson |
| D303,013 S | 8/1989 | Konopka |
| 4,857,062 A | 8/1989 | Russell |
| 4,865,592 A | 9/1989 | Rycroft |
| 4,871,463 A | 10/1989 | Taylor et al. |
| 4,898,209 A | 2/1990 | Zdeb |
| 4,909,290 A | 3/1990 | Coccia |
| 4,919,596 A | 4/1990 | Slate et al. |
| 4,927,423 A | 5/1990 | Malmborg |
| 4,931,040 A | 6/1990 | Haber et al. |
| 4,932,944 A | 6/1990 | Jagger et al. |
| 4,967,797 A | 11/1990 | Manska |
| D314,050 S | 1/1991 | Sone |
| D314,622 S | 2/1991 | Andersson et al. |
| 4,997,430 A | 3/1991 | Van der Heiden et al. |
| 5,006,114 A | 4/1991 | Rogers et al. |
| 5,035,686 A | 7/1991 | Crittenden et al. |
| 5,041,105 A | 8/1991 | D'Alo et al. |
| 5,045,066 A | 9/1991 | Scheuble et al. |
| 5,049,129 A | 9/1991 | Zdeb et al. |
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,100,394 A * | 3/1992 | Dudar .................. A61M 39/14 604/537 |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,125,915 A | 6/1992 | Berry et al. |
| D328,788 S | 8/1992 | Sagae et al. |
| D331,281 S | 11/1992 | Levine |
| 5,171,230 A | 12/1992 | Eland et al. |
| 5,181,508 A | 1/1993 | Poole, Jr. |
| 5,201,705 A | 4/1993 | Berglund et al. |
| 5,201,717 A | 4/1993 | Wyatt et al. |
| 5,203,771 A | 4/1993 | Melker et al. |
| 5,203,775 A | 4/1993 | Frank et al. |
| 5,211,638 A | 5/1993 | Dudar et al. |

(56) References Cited

U.S. PATENT DOCUMENTS

| | | |
|---|---|---|
| D337,828 S | 7/1993 | Gordon |
| 5,232,029 A | 8/1993 | Knox et al. |
| 5,232,109 A | 8/1993 | Tirrell et al. |
| 5,242,432 A | 9/1993 | Defrank |
| 5,247,972 A | 9/1993 | Tetreault |
| D341,420 S | 11/1993 | Conn |
| 5,269,768 A | 12/1993 | Cheung |
| 5,270,219 A | 12/1993 | Decastro et al. |
| 5,279,576 A | 1/1994 | Loo et al. |
| 5,288,290 A | 2/1994 | Brody |
| 5,300,034 A | 4/1994 | Behnke et al. |
| 5,301,685 A | 4/1994 | Guirguis |
| 5,304,163 A | 4/1994 | Bonnici et al. |
| 5,304,165 A | 4/1994 | Haber et al. |
| 5,308,483 A | 5/1994 | Sklar et al. |
| 5,312,377 A | 5/1994 | Dalton |
| 5,328,474 A | 7/1994 | Raines |
| D349,648 S | 8/1994 | Tirrell et al. |
| 5,334,163 A | 8/1994 | Sinnett |
| 5,334,179 A | 8/1994 | Poli et al. |
| 5,342,346 A | 8/1994 | Honda et al. |
| 5,344,417 A | 9/1994 | Wadsworth, Jr. |
| 5,348,544 A | 9/1994 | Sweeney et al. |
| 5,348,548 A | 9/1994 | Meyer et al. |
| 5,350,372 A | 9/1994 | Ikeda et al. |
| 5,364,386 A | 11/1994 | Fukuoka et al. |
| 5,364,387 A | 11/1994 | Sweeney |
| 5,374,264 A | 12/1994 | Wadsworth, Jr. |
| 5,385,547 A | 1/1995 | Wong et al. |
| 5,397,303 A | 3/1995 | Sancoff et al. |
| D357,733 S | 4/1995 | Matkovich |
| 5,429,614 A | 7/1995 | Fowles et al. |
| 5,433,330 A | 7/1995 | Yatsko et al. |
| 5,445,630 A | 8/1995 | Richmond |
| 5,445,631 A | 8/1995 | Uchida |
| D362,718 S | 9/1995 | Deily et al. |
| 5,451,374 A | 9/1995 | Molina |
| 5,454,805 A | 10/1995 | Brony |
| 5,464,111 A | 11/1995 | Vacek et al. |
| 5,464,123 A | 11/1995 | Scarrow |
| 5,466,219 A | 11/1995 | Lynn et al. |
| 5,466,220 A | 11/1995 | Brenneman |
| 5,470,327 A | 11/1995 | Helgren et al. |
| 5,471,994 A | 12/1995 | Guirguis |
| 5,472,022 A | 12/1995 | Michel et al. |
| 5,478,337 A | 12/1995 | Okamoto et al. |
| 5,482,446 A | 1/1996 | Williamson et al. |
| 5,492,147 A | 2/1996 | Challender et al. |
| 5,496,274 A | 3/1996 | Graves et al. |
| D369,406 S | 4/1996 | Niedospial et al. |
| 5,505,714 A | 4/1996 | Dassa et al. |
| 5,509,433 A | 4/1996 | Paradis |
| 5,515,871 A | 5/1996 | Bittner et al. |
| 5,520,659 A | 5/1996 | Hedges |
| 5,526,853 A | 6/1996 | Mcphee et al. |
| 5,527,306 A | 6/1996 | Haining |
| 5,531,695 A | 7/1996 | Swisher |
| 5,547,471 A | 8/1996 | Thompson et al. |
| 5,549,577 A | 8/1996 | Siegel et al. |
| 5,554,128 A | 9/1996 | Hedges |
| 5,562,686 A | 10/1996 | Sauer et al. |
| 5,562,696 A | 10/1996 | Nobles et al. |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley et al. |
| 5,603,706 A | 2/1997 | Wyatt et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,637,101 A | 6/1997 | Shillington |
| 5,641,010 A | 6/1997 | Maier |
| 5,645,538 A | 7/1997 | Richmond |
| 5,647,845 A | 7/1997 | Haber et al. |
| 5,651,776 A | 7/1997 | Appling et al. |
| 5,653,686 A | 8/1997 | Coulter et al. |
| 5,658,133 A | 8/1997 | Anderson et al. |
| 5,672,160 A | 9/1997 | Oesterlind et al. |
| 5,674,195 A | 10/1997 | Truthan |
| 5,676,346 A | 10/1997 | Einsing |
| 5,685,845 A | 11/1997 | Grimard |
| D388,172 S | 12/1997 | Cipes |
| 5,699,821 A | 12/1997 | Paradis |
| 5,702,019 A | 12/1997 | Grimard |
| 5,718,346 A | 2/1998 | Weiler |
| 5,728,087 A | 3/1998 | Niedospial |
| D393,722 S | 4/1998 | Fangrow et al. |
| 5,738,144 A | 4/1998 | Rogers |
| 5,743,312 A | 4/1998 | Pfeifer et al. |
| 5,746,733 A | 5/1998 | Capaccio et al. |
| 5,752,942 A | 5/1998 | Doyle et al. |
| 5,755,696 A | 5/1998 | Caizza |
| 5,766,211 A | 6/1998 | Wood et al. |
| 5,772,630 A | 6/1998 | Ljungquist |
| 5,772,652 A | 6/1998 | Zielinski |
| RE35,841 E | 7/1998 | Frank et al. |
| 5,776,116 A | 7/1998 | Lopez et al. |
| 5,782,872 A | 7/1998 | Muller |
| 5,806,831 A | 9/1998 | Paradis |
| 5,810,792 A | 9/1998 | Fangrow et al. |
| 5,814,020 A | 9/1998 | Gross |
| D399,558 S | 10/1998 | Guala et al. |
| D399,559 S | 10/1998 | Molina |
| 5,817,082 A | 10/1998 | Niedospial et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,833,674 A * | 11/1998 | Turnbull ............ A61M 39/045 604/533 |
| 5,834,744 A | 11/1998 | Risman |
| 5,839,715 A | 11/1998 | Leinsing |
| D403,398 S | 12/1998 | Guala et al. |
| 5,853,406 A | 12/1998 | Masuda et al. |
| D405,522 S | 2/1999 | Hoenig et al. |
| 5,868,710 A | 2/1999 | Battiato et al. |
| 5,871,110 A | 2/1999 | Grimard et al. |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,890,610 A | 4/1999 | Jansen et al. |
| 5,891,129 A | 4/1999 | Daubert et al. |
| 5,893,397 A * | 4/1999 | Peterson ............ A61J 1/2096 141/378 |
| 5,897,526 A | 4/1999 | Vaillancourt |
| 5,899,468 A | 5/1999 | Apps et al. |
| 5,902,280 A | 5/1999 | Powles et al. |
| 5,902,298 A | 5/1999 | Niedospial et al. |
| D410,740 S | 6/1999 | Molina |
| 5,911,710 A | 6/1999 | Barry et al. |
| 5,919,182 A | 7/1999 | Avallone |
| 5,921,419 A | 7/1999 | Niedospial et al. |
| 5,924,584 A | 7/1999 | Hellstrom et al. |
| 5,925,029 A | 7/1999 | Jansen et al. |
| 5,935,112 A | 8/1999 | Stevens et al. |
| 5,941,848 A | 8/1999 | Nishimoto et al. |
| 5,941,850 A | 8/1999 | Shah et al. |
| 5,944,700 A | 8/1999 | Nguyen et al. |
| D414,562 S | 9/1999 | Tajima |
| 5,954,104 A | 9/1999 | Daubert et al. |
| 5,968,022 A | 10/1999 | Saito |
| 5,971,181 A | 10/1999 | Niedospial et al. |
| 5,971,965 A | 10/1999 | Mayer |
| D416,086 S | 11/1999 | Parris et al. |
| 5,989,237 A | 11/1999 | Fowles et al. |
| D417,733 S | 12/1999 | Howell et al. |
| 6,003,566 A | 12/1999 | Thibault et al. |
| 6,004,278 A | 12/1999 | Botich et al. |
| 6,019,750 A | 2/2000 | Fowles et al. |

(56) References Cited

U.S. PATENT DOCUMENTS

| | | | |
|---|---|---|---|
| 6,022,339 A | 2/2000 | Fowles et al. |
| 6,036,171 A | 3/2000 | Weinheimer et al. |
| 6,039,093 A | 3/2000 | Mrotzek et al. |
| 6,039,302 A | 3/2000 | Cote et al. |
| D422,357 S | 4/2000 | Niedospial et al. |
| 6,053,899 A | 4/2000 | Slanda et al. |
| 6,063,068 A | 5/2000 | Fowles et al. |
| D427,308 S | 6/2000 | Zinger |
| D427,309 S | 6/2000 | Molina |
| 6,070,623 A | 6/2000 | Aneas |
| 6,071,270 A | 6/2000 | Fowles et al. |
| 6,080,132 A | 6/2000 | Cole et al. |
| D428,141 S | 7/2000 | Brotspies et al. |
| 6,086,762 A | 7/2000 | Guala |
| 6,089,541 A | 7/2000 | Weinheimer et al. |
| 6,090,091 A | 7/2000 | Fowles et al. |
| 6,090,093 A | 7/2000 | Thibault et al. |
| 6,092,692 A | 7/2000 | Riskin |
| D430,291 S | 8/2000 | Jansen et al. |
| 6,099,511 A | 8/2000 | Devos et al. |
| 6,113,068 A | 9/2000 | Ryan |
| 6,113,583 A | 9/2000 | Fowles et al. |
| 6,117,114 A | 9/2000 | Paradis |
| D431,864 S | 10/2000 | Jansen |
| 6,139,534 A * | 10/2000 | Niedospial, Jr. ...... A61J 1/2096 |
| | | | 604/414 |
| 6,142,446 A | 11/2000 | Leinsing |
| 6,146,362 A * | 11/2000 | Turnbull ............ A61M 39/045 |
| | | | 604/256 |
| 6,149,623 A | 11/2000 | Reynolds |
| 6,156,025 A | 12/2000 | Niedospial et al. |
| 6,159,192 A | 12/2000 | Fowles et al. |
| 6,162,199 A | 12/2000 | Geringer |
| 6,168,037 B1 | 1/2001 | Grimard |
| 6,171,287 B1 | 1/2001 | Lynn et al. |
| 6,171,293 B1 | 1/2001 | Rowley et al. |
| 6,173,852 B1 | 1/2001 | Browne |
| 6,173,868 B1 | 1/2001 | Dejonge |
| 6,174,304 B1 | 1/2001 | Weston |
| 6,179,822 B1 | 1/2001 | Niedospial |
| 6,179,823 B1 | 1/2001 | Niedospial |
| 6,186,997 B1 | 2/2001 | Gabbard et al. |
| 6,206,861 B1 | 3/2001 | Mayer |
| 6,221,041 B1 | 4/2001 | Russo |
| 6,221,054 B1 | 4/2001 | Martin et al. |
| 6,221,065 B1 | 4/2001 | Davis |
| 6,238,372 B1 | 5/2001 | Zinger et al. |
| 6,245,044 B1 | 6/2001 | Daw et al. |
| D445,501 S | 7/2001 | Niedospial |
| D445,895 S | 7/2001 | Svendsen |
| 6,253,804 B1 | 7/2001 | Safabash |
| 6,258,078 B1 | 7/2001 | Thilly |
| 6,280,430 B1 | 8/2001 | Neftel et al. |
| 6,290,688 B1 | 9/2001 | Lopez et al. |
| 6,296,621 B1 | 10/2001 | Masuda et al. |
| 6,299,131 B1 | 10/2001 | Ryan |
| D453,221 S | 1/2002 | Haytman et al. |
| 6,343,629 B1 | 2/2002 | Wessman et al. |
| 6,348,044 B1 | 2/2002 | Coletti et al. |
| 6,358,236 B1 | 3/2002 | Defoggi et al. |
| 6,364,866 B1 | 4/2002 | Furr et al. |
| 6,378,576 B2 | 4/2002 | Thibault et al. |
| 6,378,714 B1 | 4/2002 | Jansen et al. |
| 6,379,340 B1 | 4/2002 | Zinger et al. |
| D457,954 S | 5/2002 | Wallace et al. |
| 6,382,442 B1 | 5/2002 | Thibault et al. |
| 6,386,397 B2 | 5/2002 | Brotspies et al. |
| 6,408,897 B1 | 6/2002 | Laurent et al. |
| 6,409,708 B1 | 6/2002 | Wessman |
| 6,419,696 B1 | 7/2002 | Ortiz et al. |
| 6,440,107 B1 | 8/2002 | Trombley et al. |
| 6,453,949 B1 | 9/2002 | Chau |
| 6,453,956 B2 | 9/2002 | Safabash |
| 6,474,375 B2 | 11/2002 | Spero et al. |
| 6,478,788 B1 | 11/2002 | Aneas |
| D468,015 S | 12/2002 | Horppu |
| 6,499,617 B1 | 12/2002 | Niedospial et al. |
| 6,503,240 B1 | 1/2003 | Niedospial et al. |
| 6,503,244 B2 | 1/2003 | Hayman |
| 6,520,932 B2 | 2/2003 | Taylor |
| 6,524,278 B1 | 2/2003 | Campbell et al. |
| 6,524,295 B2 | 2/2003 | Daubert et al. |
| D472,316 S | 3/2003 | Douglas et al. |
| 6,530,903 B2 | 3/2003 | Wang et al. |
| 6,537,263 B1 | 3/2003 | Aneas |
| D472,630 S | 4/2003 | Douglas et al. |
| 6,544,246 B1 | 4/2003 | Niedospial |
| 6,551,299 B2 | 4/2003 | Miyoshi et al. |
| 6,558,365 B2 | 5/2003 | Zinger et al. |
| 6,569,196 B1 | 5/2003 | Vesely |
| 6,571,837 B2 | 6/2003 | Jansen et al. |
| 6,572,591 B2 | 6/2003 | Mayer |
| 6,575,955 B2 | 6/2003 | Azzolini |
| 6,581,593 B1 | 6/2003 | Rubin et al. |
| 6,581,648 B1 | 6/2003 | Zolentroff et al. |
| 6,582,415 B1 * | 6/2003 | Fowles .................. A61J 1/2089 |
| | | | 137/614.04 |
| D476,731 S | 7/2003 | Cise et al. |
| 6,591,876 B2 | 7/2003 | Safabash |
| 6,599,273 B1 | 7/2003 | Lopez |
| 6,601,721 B2 | 8/2003 | Jansen et al. |
| 6,626,309 B1 | 9/2003 | Jansen et al. |
| 6,632,201 B1 | 10/2003 | Mathias et al. |
| 6,638,244 B1 | 10/2003 | Reynolds |
| D482,121 S | 11/2003 | Harding et al. |
| D482,447 S | 11/2003 | Harding et al. |
| 6,651,956 B2 | 11/2003 | Miller |
| 6,652,509 B1 | 11/2003 | Helgren et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial |
| 6,681,810 B2 | 1/2004 | Weston |
| 6,681,946 B1 | 1/2004 | Jansen et al. |
| 6,682,509 B2 | 1/2004 | Lopez |
| 6,692,478 B1 | 2/2004 | Paradis |
| 6,692,829 B2 | 2/2004 | Stubler et al. |
| 6,695,829 B2 | 2/2004 | Hellstrom et al. |
| 6,699,229 B2 | 3/2004 | Zinger et al. |
| 6,699,232 B2 | 3/2004 | Hart et al. |
| 6,706,022 B1 | 3/2004 | Leinsing et al. |
| 6,706,031 B2 | 3/2004 | Manera |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,746,438 B1 | 6/2004 | Arnissolle |
| 6,752,180 B2 | 6/2004 | Delay |
| D495,416 S | 8/2004 | Dimeo et al. |
| D496,457 S | 9/2004 | Prais et al. |
| 6,802,490 B2 | 10/2004 | Leinsing et al. |
| 6,832,994 B2 | 12/2004 | Niedospial et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,884,253 B1 | 4/2005 | Mcfarlane |
| 6,890,328 B2 | 5/2005 | Fowles et al. |
| D506,256 S | 6/2005 | Miyoshi et al. |
| 6,901,975 B2 | 6/2005 | Aramata et al. |
| 6,945,417 B2 | 9/2005 | Jansen et al. |
| 6,948,522 B2 | 9/2005 | Newbrough et al. |
| 6,949,086 B2 | 9/2005 | Ferguson et al. |
| 6,951,613 B2 | 10/2005 | Reif et al. |
| 6,953,450 B2 | 10/2005 | Baldwin et al. |
| 6,957,745 B2 | 10/2005 | Thibault et al. |
| 6,960,164 B2 | 11/2005 | O'Heeron |
| 6,964,684 B2 | 11/2005 | Ortiz et al. |
| 6,972,002 B2 | 12/2005 | Thorne |
| 6,979,318 B1 | 12/2005 | Mcdonald et al. |
| RE38,996 E | 2/2006 | Crawford et al. |
| 6,994,315 B2 | 2/2006 | Ryan et al. |
| 6,997,916 B2 | 2/2006 | Simas et al. |
| 6,997,917 B2 | 2/2006 | Niedospial et al. |

(56) References Cited

U.S. PATENT DOCUMENTS

| | | |
|---|---|---|
| 7,024,968 B2 | 4/2006 | Raudabough et al. |
| 7,070,589 B2 | 7/2006 | Lolachi et al. |
| 7,074,216 B2 | 7/2006 | Fowles et al. |
| 7,083,600 B2 | 8/2006 | Meloul |
| 7,086,431 B2 | 8/2006 | D'Antonio et al. |
| 7,097,637 B2 | 8/2006 | Triplett et al. |
| 7,100,890 B2 | 9/2006 | Cote et al. |
| 7,140,401 B2 | 11/2006 | Wilcox et al. |
| 7,150,735 B2 | 12/2006 | Hickle |
| 7,192,423 B2 | 3/2007 | Wong |
| 7,195,623 B2 | 3/2007 | Burroughs et al. |
| D546,450 S | 7/2007 | Wolf |
| 7,241,285 B1 | 7/2007 | Dikeman |
| 7,294,122 B2 | 11/2007 | Kubo et al. |
| 7,306,199 B2 | 12/2007 | Leinsing et al. |
| D560,815 S | 1/2008 | Tajima |
| D561,348 S | 2/2008 | Zinger et al. |
| 7,326,188 B1 | 2/2008 | Russell et al. |
| 7,326,194 B2 | 2/2008 | Zinger et al. |
| 7,335,213 B1 | 2/2008 | Hyde et al. |
| 7,350,764 B2 | 4/2008 | Raybuck |
| 7,354,422 B2 | 4/2008 | Riesenberger et al. |
| 7,354,427 B2 | 4/2008 | Fangrow |
| D573,250 S | 7/2008 | Macrae et al. |
| D575,314 S | 8/2008 | Hind |
| 7,425,209 B2 | 9/2008 | Fowles et al. |
| 7,435,246 B2 | 10/2008 | Zihlmann |
| D580,558 S | 11/2008 | Shigesada et al. |
| D581,529 S | 11/2008 | Moehle et al. |
| 7,452,348 B2 | 11/2008 | Hasegawa |
| 7,470,257 B2 | 12/2008 | Norton et al. |
| 7,470,265 B2 | 12/2008 | Brugger et al. |
| 7,472,932 B2 | 1/2009 | Weber et al. |
| 7,488,297 B2 | 2/2009 | Flaherty |
| 7,491,197 B2 | 2/2009 | Jansen et al. |
| 7,497,848 B2 | 3/2009 | Leinsing et al. |
| 7,500,961 B2 | 3/2009 | Nemoto |
| 7,523,967 B2 | 4/2009 | Steppe |
| 7,530,546 B2 | 5/2009 | Ryan et al. |
| D595,420 S | 6/2009 | Suzuki et al. |
| D595,421 S | 6/2009 | Suzuki et al. |
| 7,540,863 B2 | 6/2009 | Haindl |
| 7,540,865 B2 | 6/2009 | Griffin et al. |
| 7,544,191 B2 | 6/2009 | Peluso et al. |
| D595,862 S | 7/2009 | Suzuki et al. |
| D595,863 S | 7/2009 | Suzuki et al. |
| 7,569,062 B1 | 8/2009 | Kuehn et al. |
| D604,837 S | 11/2009 | Crawford et al. |
| 7,611,487 B2 | 11/2009 | Woehr et al. |
| 7,611,502 B2 | 11/2009 | Daly |
| 7,615,041 B2 | 11/2009 | Sullivan et al. |
| 7,628,779 B2 | 12/2009 | Aneas |
| 7,632,261 B2 | 12/2009 | Zinger et al. |
| D608,900 S | 1/2010 | Giraud et al. |
| D609,804 S | 2/2010 | Uchida et al. |
| 7,654,995 B2 | 2/2010 | Warren et al. |
| 7,670,326 B2 | 3/2010 | Shemesh |
| 7,695,445 B2 | 4/2010 | Yuki |
| 7,703,483 B2 | 4/2010 | Hartman et al. |
| 7,704,229 B2 | 4/2010 | Moberg et al. |
| 7,704,236 B2 | 4/2010 | Denolly |
| D616,090 S | 5/2010 | Kawamura |
| 7,713,247 B2 | 5/2010 | Lopez |
| 7,717,886 B2 | 5/2010 | Lopez |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosler et al. |
| 7,744,581 B2 | 6/2010 | Wallen et al. |
| 7,757,901 B2 | 7/2010 | Welp |
| 7,758,082 B2 | 7/2010 | Weigel et al. |
| 7,758,560 B2 | 7/2010 | Connell et al. |
| 7,762,524 B2 | 7/2010 | Cawthon et al. |
| 7,766,304 B2 | 8/2010 | Phillips |
| 7,771,383 B2 | 8/2010 | Truitt et al. |
| D624,641 S | 9/2010 | Boclet |
| 7,799,009 B2 | 9/2010 | Niedospial et al. |
| 7,803,140 B2 | 9/2010 | Fangrow, Jr. |
| D627,216 S | 11/2010 | Fulginiti |
| D630,732 S | 1/2011 | Lev et al. |
| 7,862,537 B2 | 1/2011 | Zinger et al. |
| 7,867,215 B2 | 1/2011 | Akerlund et al. |
| 7,879,018 B2 | 2/2011 | Zinger et al. |
| 7,883,499 B2 | 2/2011 | Fangrow |
| 7,887,583 B2 | 2/2011 | Macoviak |
| 7,895,216 B2 | 2/2011 | Longshaw et al. |
| D634,007 S | 3/2011 | Zinger et al. |
| 7,896,849 B2 | 3/2011 | Delay |
| 7,900,659 B2 | 3/2011 | Whitley et al. |
| 7,914,499 B2 | 3/2011 | Gonnelli et al. |
| D637,713 S | 5/2011 | Nord et al. |
| 7,963,954 B2 | 6/2011 | Kavazov |
| D641,080 S | 7/2011 | Zinger et al. |
| 7,985,216 B2 | 7/2011 | Daily et al. |
| D644,104 S | 8/2011 | Maeda et al. |
| 7,993,328 B2 | 8/2011 | Whitley |
| 8,007,461 B2 | 8/2011 | Huo et al. |
| 8,012,132 B2 | 9/2011 | Lum et al. |
| 8,016,809 B2 | 9/2011 | Zinger et al. |
| 8,021,325 B2 | 9/2011 | Zinger et al. |
| 8,025,653 B2 | 9/2011 | Capitaine et al. |
| 8,025,683 B2 | 9/2011 | Morrison |
| 8,029,472 B2 | 10/2011 | Leinsing et al. |
| 8,038,123 B2 | 10/2011 | Ruschke et al. |
| 8,066,688 B2 | 11/2011 | Zinger et al. |
| 8,070,739 B2 | 12/2011 | Zinger et al. |
| 8,075,550 B2 | 12/2011 | Nord et al. |
| 8,096,525 B2 | 1/2012 | Ryan |
| 8,105,314 B2 | 1/2012 | Fangrow, Jr. |
| D654,166 S | 2/2012 | Lair |
| D655,017 S | 2/2012 | Mosler et al. |
| 8,122,923 B2 | 2/2012 | Kraus et al. |
| 8,123,736 B2 | 2/2012 | Kraushaar et al. |
| D655,071 S | 3/2012 | Davila |
| D657,461 S | 4/2012 | Schembre et al. |
| 8,152,779 B2 | 4/2012 | Cabiri |
| 8,157,784 B2 | 4/2012 | Rogers |
| 8,167,863 B2 | 5/2012 | Yow |
| 8,172,824 B2 | 5/2012 | Pfeifer et al. |
| 8,177,768 B2 | 5/2012 | Leinsing |
| 8,182,452 B2 | 5/2012 | Mansour et al. |
| 8,187,248 B2 | 5/2012 | Zihlmann |
| 8,196,614 B2 * | 6/2012 | Kriheli ................. B65D 51/002 141/330 |
| 8,197,459 B2 | 6/2012 | Jansen et al. |
| 8,211,069 B2 | 7/2012 | Fangrow, Jr. |
| 8,225,959 B2 | 7/2012 | Lambrecht |
| 8,241,268 B2 | 8/2012 | Whitley |
| 8,262,628 B2 | 9/2012 | Fangrow, Jr. |
| 8,262,641 B2 | 9/2012 | Vedrine et al. |
| 8,267,127 B2 | 9/2012 | Kriheli |
| D669,980 S | 10/2012 | Lev et al. |
| 8,287,513 B2 | 10/2012 | Ellstrom et al. |
| D671,654 S | 11/2012 | Akamatsu et al. |
| 8,317,741 B2 | 11/2012 | Kraushaar |
| 8,328,784 B2 | 12/2012 | Jensen et al. |
| D673,673 S | 1/2013 | Wang |
| D674,084 S | 1/2013 | Linnenschmidt |
| D674,088 S | 1/2013 | Lev et al. |
| 8,348,898 B2 | 1/2013 | Cabiri |
| D681,230 S | 4/2013 | Mosler et al. |
| 8,418,690 B2 | 4/2013 | Power et al. |
| 8,454,573 B2 | 6/2013 | Wyatt et al. |
| 8,469,939 B2 | 6/2013 | Fangrow, Jr. |
| 8,475,404 B2 | 7/2013 | Foshee et al. |
| 8,480,645 B1 | 7/2013 | Choudhury et al. |
| 8,480,646 B2 | 7/2013 | Nord et al. |
| 8,506,548 B2 | 8/2013 | Okiyama |
| 8,511,352 B2 | 8/2013 | Kraus et al. |
| 8,512,309 B2 | 8/2013 | Shemesh et al. |
| D689,605 S | 9/2013 | Bellenoit |
| D690,009 S | 9/2013 | Schembre et al. |
| D690,418 S | 9/2013 | Rosenquist |
| 8,523,837 B2 | 9/2013 | Wiggins et al. |

(56) References Cited

U.S. PATENT DOCUMENTS

| | | | |
|---|---|---|---|
| D691,264 S | 10/2013 | Dallemagne et al. |
| 8,545,476 B2 | 10/2013 | Ariagno et al. |
| 8,551,067 B2 | 10/2013 | Zinger et al. |
| 8,556,879 B2 | 10/2013 | Okiyama |
| 8,562,582 B2 | 10/2013 | Tuckwell et al. |
| 8,608,723 B2 | 12/2013 | Lev et al. |
| 8,628,508 B2 | 1/2014 | Weitzel et al. |
| 8,636,689 B2 | 1/2014 | Halili et al. |
| D703,812 S | 4/2014 | Cederschiold et al. |
| 8,684,992 B2 | 4/2014 | Sullivan et al. |
| 8,684,994 B2 | 4/2014 | Lev et al. |
| 8,752,598 B2 | 6/2014 | Denenburg et al. |
| D714,935 S | 10/2014 | Nishioka et al. |
| D717,406 S | 11/2014 | Stanley et al. |
| D717,948 S | 11/2014 | Strong et al. |
| D719,650 S | 12/2014 | Arinobe et al. |
| D720,067 S | 12/2014 | Rosenquist |
| D720,451 S | 12/2014 | Denenburg et al. |
| D720,452 S | 12/2014 | Jordan |
| 8,900,212 B2 | 12/2014 | Kubo |
| 8,905,994 B1 | 12/2014 | Lev et al. |
| 8,915,882 B2 | 12/2014 | Cabiri |
| D720,850 S | 1/2015 | Hsia et al. |
| 8,986,370 B2 | 3/2015 | Annest |
| 9,011,522 B2 | 4/2015 | Annest |
| D732,660 S | 6/2015 | Ohashi |
| D732,664 S | 6/2015 | Woehr et al. |
| D733,291 S | 6/2015 | Wang |
| D733,292 S | 6/2015 | Rogers |
| D733,293 S | 6/2015 | Rogers |
| 9,072,827 B2 | 7/2015 | Cabiri |
| D738,494 S | 9/2015 | Kashmirian |
| D741,457 S | 10/2015 | Guest |
| 9,149,575 B2 | 10/2015 | Cabiri |
| D750,235 S | 2/2016 | Maurice |
| 9,254,242 B2 | 2/2016 | Mueller et al. |
| D757,933 S | 5/2016 | Lev et al. |
| 9,393,365 B2 | 7/2016 | Cabiri |
| D765,837 S | 9/2016 | Lev et al. |
| D767,124 S | 9/2016 | Lev et al. |
| 9,486,391 B2 | 11/2016 | Shemesh |
| 9,492,610 B2 | 11/2016 | Cabiri |
| 9,511,190 B2 | 12/2016 | Cabiri |
| 9,522,234 B2 | 12/2016 | Cabiri |
| D794,183 S | 8/2017 | Lev et al. |
| 9,763,855 B2 | 9/2017 | Fangrow |
| D833,599 S | 11/2018 | Nilsson et al. |
| D836,324 S | 12/2018 | Michalski |
| 10,206,854 B2 | 2/2019 | Wu et al. |
| D849,936 S | 5/2019 | Allard |
| D851,240 S | 6/2019 | Baid |
| 10,413,662 B2 | 9/2019 | Yeh et al. |
| D881,389 S | 4/2020 | Wang et al. |
| D881,390 S | 4/2020 | Wang et al. |
| 10,772,798 B2 | 9/2020 | Lev et al. |
| D903,836 S | 12/2020 | Pak et al. |
| D923,782 S | 6/2021 | Lev et al. |
| D923,812 S | 6/2021 | Ben Shalom |
| 2001/0000347 A1 | 4/2001 | Hellstrom et al. |
| 2001/0025671 A1 | 10/2001 | Safabash |
| 2001/0029360 A1 | 10/2001 | Miyoshi et al. |
| 2001/0047150 A1 | 11/2001 | Chobotov |
| 2001/0051793 A1 | 12/2001 | Weston |
| 2002/0017328 A1 | 2/2002 | Loo |
| 2002/0029080 A1 | 3/2002 | Mortier et al. |
| 2002/0055711 A1 | 5/2002 | Lavi et al. |
| 2002/0065488 A1 | 5/2002 | Suzuki et al. |
| 2002/0066715 A1 | 6/2002 | Niedospial |
| 2002/0087118 A1 | 7/2002 | Reynolds et al. |
| 2002/0087141 A1 | 7/2002 | Zinger et al. |
| 2002/0087144 A1 | 7/2002 | Zinger et al. |
| 2002/0104584 A1 | 8/2002 | Spero et al. |
| 2002/0115980 A1 | 8/2002 | Niedospial et al. |
| 2002/0121496 A1 | 9/2002 | Thiebault et al. |
| 2002/0123736 A1 | 9/2002 | Fowles et al. |
| 2002/0123737 A1 | 9/2002 | Hart et al. |
| 2002/0127150 A1 | 9/2002 | Sasso |
| 2002/0128628 A1 | 9/2002 | Fathallah |
| 2002/0138045 A1 | 9/2002 | Moen |
| 2002/0173752 A1 | 11/2002 | Polzin |
| 2002/0193777 A1 | 12/2002 | Aneas |
| 2003/0028156 A1 | 2/2003 | Juliar |
| 2003/0036725 A1 | 2/2003 | Lavi et al. |
| 2003/0068354 A1 | 4/2003 | Reif et al. |
| 2003/0069550 A1 | 4/2003 | Sharp |
| 2003/0073971 A1 | 4/2003 | Saker |
| 2003/0083742 A1 | 5/2003 | Spence et al. |
| 2003/0100866 A1 | 5/2003 | Reynolds |
| 2003/0109846 A1 | 6/2003 | Zinger et al. |
| 2003/0120209 A1 | 6/2003 | Jensen et al. |
| 2003/0135159 A1 | 7/2003 | Daily et al. |
| 2003/0153895 A1 | 8/2003 | Leinsing |
| 2003/0187420 A1 | 10/2003 | Akerlund et al. |
| 2003/0191445 A1 | 10/2003 | Wallen et al. |
| 2003/0195479 A1 | 10/2003 | Kuracina et al. |
| 2003/0199827 A1 | 10/2003 | Thorne |
| 2003/0199846 A1 | 10/2003 | Fowles et al. |
| 2003/0199847 A1 | 10/2003 | Akerlund et al. |
| 2003/0205843 A1 | 11/2003 | Adams |
| 2003/0236543 A1 | 12/2003 | Brenneman et al. |
| 2004/0010207 A1 | 1/2004 | Flaherty et al. |
| 2004/0024354 A1 | 2/2004 | Reynolds |
| 2004/0039365 A1 | 2/2004 | Aramata et al. |
| 2004/0044327 A1 | 3/2004 | Hasegawa |
| 2004/0044406 A1 | 3/2004 | Woolfson et al. |
| 2004/0073189 A1* | 4/2004 | Wyatt .................. A61M 5/162 604/905 |
| 2004/0143218 A1 | 7/2004 | Das |
| 2004/0143226 A1 | 7/2004 | Marsden |
| 2004/0153047 A1 | 8/2004 | Blank et al. |
| 2004/0158172 A1 | 8/2004 | Hancock |
| 2004/0162515 A1 | 8/2004 | Chornenky et al. |
| 2004/0162540 A1 | 8/2004 | Walenciak et al. |
| 2004/0167472 A1 | 8/2004 | Howell et al. |
| 2004/0167620 A1 | 8/2004 | Ortiz et al. |
| 2004/0181192 A1 | 9/2004 | Cuppy |
| 2004/0186424 A1 | 9/2004 | Hjertman |
| 2004/0199139 A1 | 10/2004 | Fowles et al. |
| 2004/0204699 A1 | 10/2004 | Hanly et al. |
| 2004/0217315 A1 | 11/2004 | Doyle |
| 2004/0225274 A1 | 11/2004 | Jansen et al. |
| 2004/0236305 A1 | 11/2004 | Jansen et al. |
| 2004/0236419 A1 | 11/2004 | Milo |
| 2004/0249341 A1 | 12/2004 | Newbrough et al. |
| 2004/0255952 A1 | 12/2004 | Carlsen et al. |
| 2005/0010287 A1 | 1/2005 | Macoviak et al. |
| 2005/0015070 A1 | 1/2005 | Delnevo et al. |
| 2005/0016626 A1 | 1/2005 | Wilcox et al. |
| 2005/0049553 A1 | 3/2005 | Triplett et al. |
| 2005/0055008 A1 | 3/2005 | Paradis et al. |
| 2005/0070999 A1 | 3/2005 | Spence |
| 2005/0075727 A1 | 4/2005 | Wheatley |
| 2005/0082828 A1 | 4/2005 | Wicks et al. |
| 2005/0124964 A1 | 6/2005 | Niedospial et al. |
| 2005/0137523 A1 | 6/2005 | Wyatt et al. |
| 2005/0137566 A1 | 6/2005 | Fowles et al. |
| 2005/0137702 A1 | 6/2005 | Haug et al. |
| 2005/0148994 A1 | 7/2005 | Leinsing |
| 2005/0159706 A1 | 7/2005 | Wilkinson et al. |
| 2005/0159724 A1 | 7/2005 | Enerson |
| 2005/0182383 A1 | 8/2005 | Wallen |
| 2005/0209554 A1 | 9/2005 | Landau |
| 2005/0261637 A1 | 11/2005 | Miller |
| 2005/0277896 A1 | 12/2005 | Messerli et al. |
| 2006/0030832 A1 | 2/2006 | Niedospial et al. |
| 2006/0049209 A1 | 3/2006 | Baker |
| 2006/0058741 A1 | 3/2006 | Gallagher |
| 2006/0074484 A1 | 4/2006 | Huber |
| 2006/0079834 A1* | 4/2006 | Tennican ............... A61M 5/284 206/363 |
| 2006/0089594 A1 | 4/2006 | Landau |
| 2006/0089603 A1 | 4/2006 | Truitt et al. |
| 2006/0095015 A1 | 5/2006 | Hobbs et al. |
| 2006/0106360 A1 | 5/2006 | Wong |

(56) References Cited

U.S. PATENT DOCUMENTS

| | | |
|---|---|---|
| 2006/0135948 A1 | 6/2006 | Varma |
| 2006/0155257 A1 | 7/2006 | Reynolds |
| 2006/0161192 A1 | 7/2006 | Young |
| 2006/0169348 A1 | 8/2006 | Yigal |
| 2006/0173410 A1 | 8/2006 | Moberg et al. |
| 2006/0178646 A1 | 8/2006 | Harris et al. |
| 2006/0195029 A1 | 8/2006 | Shults et al. |
| 2006/0212004 A1 | 9/2006 | Atil |
| 2006/0224105 A1 | 10/2006 | Thorne et al. |
| 2006/0253084 A1 | 11/2006 | Nordgren |
| 2006/0259004 A1 | 11/2006 | Connell et al. |
| 2006/0259135 A1 | 11/2006 | Navia et al. |
| 2006/0287639 A1* | 12/2006 | Sharp .................. A61J 1/2096 604/415 |
| 2007/0016381 A1 | 1/2007 | Kamath et al. |
| 2007/0024995 A1 | 2/2007 | Hayashi |
| 2007/0060904 A1 | 3/2007 | Vedrine et al. |
| 2007/0078428 A1 | 4/2007 | Reynolds et al. |
| 2007/0079894 A1 | 4/2007 | Kraus et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0095856 A1 | 5/2007 | Vogel et al. |
| 2007/0106218 A1 | 5/2007 | Yodfat et al. |
| 2007/0106244 A1 | 5/2007 | Mosler et al. |
| 2007/0112324 A1 | 5/2007 | Hamedi-Sangsari |
| 2007/0156112 A1* | 7/2007 | Walsh .................. A61J 1/2096 604/415 |
| 2007/0167904 A1 | 7/2007 | Zinger et al. |
| 2007/0167912 A1 | 7/2007 | Causey et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0203451 A1 | 8/2007 | Murakami et al. |
| 2007/0219483 A1 | 9/2007 | Kitani et al. |
| 2007/0244447 A1 | 10/2007 | Capitaine et al. |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0249995 A1 | 10/2007 | Van |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2007/0299404 A1 | 12/2007 | Katoh et al. |
| 2008/0009789 A1 | 1/2008 | Zinger et al. |
| 2008/0009822 A1 | 1/2008 | Enerson |
| 2008/0015496 A1 | 1/2008 | Hamedi-Sangsari |
| 2008/0039935 A1 | 2/2008 | Buch et al. |
| 2008/0077235 A1 | 3/2008 | Kirson |
| 2008/0125860 A1 | 5/2008 | Webler et al. |
| 2008/0135051 A1 | 6/2008 | Lee |
| 2008/0142388 A1* | 6/2008 | Whitley ................ A61J 1/2096 206/438 |
| 2008/0167713 A1 | 7/2008 | Bolling |
| 2008/0172024 A1 | 7/2008 | Yow |
| 2008/0188799 A1 | 8/2008 | Mueller-Beckhaus et al. |
| 2008/0195049 A1 | 8/2008 | Thalmann et al. |
| 2008/0208138 A1 | 8/2008 | Lim et al. |
| 2008/0215015 A1 | 9/2008 | Cindrich et al. |
| 2008/0249473 A1 | 10/2008 | Rutti et al. |
| 2008/0249479 A1 | 10/2008 | Zinger et al. |
| 2008/0249498 A1 | 10/2008 | Fangrow |
| 2008/0262465 A1* | 10/2008 | Zinger .................. A61M 5/162 604/411 |
| 2008/0262609 A1 | 10/2008 | Gross et al. |
| 2008/0269687 A1 | 10/2008 | Chong et al. |
| 2008/0275407 A1 | 11/2008 | Scheurer |
| 2008/0287905 A1 | 11/2008 | Hiejima et al. |
| 2008/0294100 A1 | 11/2008 | De et al. |
| 2008/0306439 A1 | 12/2008 | Nelson et al. |
| 2008/0312634 A1 | 12/2008 | Helmerson et al. |
| 2009/0012492 A1 | 1/2009 | Zihlmann |
| 2009/0043253 A1 | 2/2009 | Podaima |
| 2009/0054834 A1 | 2/2009 | Zinger et al. |
| 2009/0054852 A1 | 2/2009 | Takano et al. |
| 2009/0054969 A1 | 2/2009 | Salahieh et al. |
| 2009/0062767 A1 | 3/2009 | Van et al. |
| 2009/0076360 A1 | 3/2009 | Brister et al. |
| 2009/0082750 A1 | 3/2009 | Denenburg et al. |
| 2009/0139724 A1 | 6/2009 | Gray et al. |
| 2009/0143758 A1 | 6/2009 | Okiyama |
| 2009/0177177 A1 | 7/2009 | Zinger et al. |
| 2009/0177178 A1 | 7/2009 | Pedersen |
| 2009/0187140 A1 | 7/2009 | Racz |
| 2009/0216103 A1 | 8/2009 | Brister et al. |
| 2009/0216212 A1* | 8/2009 | Fangrow, Jr. .......... A61J 1/2096 604/406 |
| 2009/0257306 A1 | 10/2009 | Coffeen et al. |
| 2009/0267011 A1 | 10/2009 | Hatton et al. |
| 2009/0299325 A1 | 12/2009 | Vedrine et al. |
| 2009/0318946 A1 | 12/2009 | Tamesada |
| 2009/0326506 A1 | 12/2009 | Hasegawa et al. |
| 2010/0010443 A1 | 1/2010 | Morgan et al. |
| 2010/0016811 A1 | 1/2010 | Smith |
| 2010/0022985 A1 | 1/2010 | Sullivan et al. |
| 2010/0030181 A1 | 2/2010 | Helle et al. |
| 2010/0036319 A1 | 2/2010 | Drake et al. |
| 2010/0042147 A1 | 2/2010 | Janovsky et al. |
| 2010/0049315 A1 | 2/2010 | Kirson |
| 2010/0070027 A1 | 3/2010 | Bonhoeffer et al. |
| 2010/0076397 A1 | 3/2010 | Reed et al. |
| 2010/0087786 A1 | 4/2010 | Zinger et al. |
| 2010/0137827 A1 | 6/2010 | Warren et al. |
| 2010/0137831 A1 | 6/2010 | Tsals |
| 2010/0152658 A1 | 6/2010 | Hanson et al. |
| 2010/0160889 A1 | 6/2010 | Smith et al. |
| 2010/0161047 A1 | 6/2010 | Cabiri |
| 2010/0162548 A1 | 7/2010 | Leidig |
| 2010/0168664 A1 | 7/2010 | Zinger et al. |
| 2010/0168712 A1 | 7/2010 | Tuckwell et al. |
| 2010/0179506 A1 | 7/2010 | Shemesh et al. |
| 2010/0198148 A1 | 8/2010 | Zinger et al. |
| 2010/0204670 A1 | 8/2010 | Kraushaar et al. |
| 2010/0228220 A1 | 9/2010 | Zinger et al. |
| 2010/0241088 A1 | 9/2010 | Ranalletta et al. |
| 2010/0262232 A1 | 10/2010 | Annest |
| 2010/0274184 A1 | 10/2010 | Chun |
| 2010/0274202 A1 | 10/2010 | Hyde et al. |
| 2010/0286661 A1 | 11/2010 | Raday et al. |
| 2010/0305548 A1 | 12/2010 | Kraushaar |
| 2010/0312220 A1 | 12/2010 | Kalitzki |
| 2011/0004143 A1 | 1/2011 | Beiriger et al. |
| 2011/0004184 A1 | 1/2011 | Proksch et al. |
| 2011/0044850 A1 | 2/2011 | Solomon et al. |
| 2011/0054440 A1 | 3/2011 | Lewis |
| 2011/0087164 A1 | 4/2011 | Mosler et al. |
| 2011/0125056 A1 | 5/2011 | Merchant |
| 2011/0144584 A1 | 6/2011 | Wozencroft |
| 2011/0160655 A1 | 6/2011 | Hanson et al. |
| 2011/0160701 A1 | 6/2011 | Wyatt et al. |
| 2011/0172636 A1 | 7/2011 | Aasmul |
| 2011/0175347 A1 | 7/2011 | Okiyama |
| 2011/0218511 A1 | 9/2011 | Yokoyama |
| 2011/0224640 A1* | 9/2011 | Kuhn .................. B65D 51/002 604/414 |
| 2011/0230856 A1 | 9/2011 | Kyle et al. |
| 2011/0264037 A1* | 10/2011 | Foshee .................. A61M 11/00 604/82 |
| 2011/0264069 A1 | 10/2011 | Bochenko |
| 2011/0275988 A1 | 11/2011 | Davis et al. |
| 2011/0276007 A1 | 11/2011 | Denenburg |
| 2011/0319827 A1 | 12/2011 | Leinsing et al. |
| 2012/0022344 A1 | 1/2012 | Kube |
| 2012/0022469 A1 | 1/2012 | Alpert |
| 2012/0053555 A1 | 3/2012 | Ariagno et al. |
| 2012/0059332 A1 | 3/2012 | Woehr et al. |
| 2012/0059346 A1 | 3/2012 | Sheppard et al. |
| 2012/0067429 A1 | 3/2012 | Mosler et al. |
| 2012/0071819 A1 | 3/2012 | Brueggemann et al. |
| 2012/0078214 A1 | 3/2012 | Finke et al. |
| 2012/0123382 A1 | 5/2012 | Kubo |

(56) References Cited

U.S. PATENT DOCUMENTS

| | | |
|---|---|---|
| 2012/0184938 A1 | 7/2012 | Lev et al. |
| 2012/0215182 A1 | 8/2012 | Mansour et al. |
| 2012/0220977 A1 | 8/2012 | Yow |
| 2012/0220978 A1* | 8/2012 | Lev ............... A61J 1/2096 604/414 |
| 2012/0265163 A1 | 10/2012 | Cheng et al. |
| 2012/0271229 A1 | 10/2012 | Lev et al. |
| 2012/0296307 A1 | 11/2012 | Holt et al. |
| 2012/0310203 A1 | 12/2012 | Khaled et al. |
| 2012/0323172 A1 | 12/2012 | Lev et al. |
| 2012/0323187 A1 | 12/2012 | Iwase et al. |
| 2012/0323210 A1* | 12/2012 | Lev ............... A61J 1/2096 604/405 |
| 2013/0046269 A1* | 2/2013 | Lev ............... A61J 1/2096 604/405 |
| 2013/0053814 A1 | 2/2013 | Mueller-Beckhaus et al. |
| 2013/0096493 A1 | 4/2013 | Kubo et al. |
| 2013/0110049 A1 | 5/2013 | Cronenberg et al. |
| 2013/0144248 A1 | 6/2013 | Putter et al. |
| 2013/0199669 A1 | 8/2013 | Moy et al. |
| 2013/0226100 A1 | 8/2013 | Lev |
| 2013/0231630 A1 | 9/2013 | Kraus et al. |
| 2013/0237904 A1 | 9/2013 | Deneburg et al. |
| 2013/0253448 A1 | 9/2013 | Baron et al. |
| 2013/0289530 A1 | 10/2013 | Wyatt et al. |
| 2013/0315026 A1 | 11/2013 | Cheio et al. |
| 2013/0317472 A1 | 11/2013 | Finke |
| 2014/0020793 A1* | 1/2014 | Denenburg ......... A61J 1/2089 141/329 |
| 2014/0096862 A1 | 4/2014 | Aneas |
| 2014/0102552 A1 | 4/2014 | Shemesh |
| 2014/0150911 A1 | 6/2014 | Hanner et al. |
| 2014/0194854 A1 | 7/2014 | Tsals |
| 2014/0221940 A1 | 8/2014 | Clauson et al. |
| 2014/0276215 A1 | 9/2014 | Nelson et al. |
| 2014/0277052 A1 | 9/2014 | Haselby et al. |
| 2014/0352845 A1* | 12/2014 | Lev ............... A61J 1/20 141/383 |
| 2015/0082746 A1 | 3/2015 | Ivosevic et al. |
| 2015/0088078 A1 | 3/2015 | Lev et al. |
| 2015/0112297 A1 | 4/2015 | Lev et al. |
| 2015/0209230 A1 | 7/2015 | Lev et al. |
| 2015/0250681 A1* | 9/2015 | Lev ............... A61J 1/201 604/414 |
| 2015/0290390 A1 | 10/2015 | Ring et al. |
| 2015/0297462 A1* | 10/2015 | Lev ............... A61J 1/201 604/407 |
| 2015/0297839 A1 | 10/2015 | Sanders et al. |
| 2015/0297880 A1 | 10/2015 | Ogawa et al. |
| 2015/0305770 A1 | 10/2015 | Fill et al. |
| 2016/0051444 A1* | 2/2016 | Muth ............... B31B 50/64 604/408 |
| 2016/0081308 A1 | 3/2016 | Cary et al. |
| 2016/0081878 A1 | 3/2016 | Marks et al. |
| 2016/0088995 A1 | 3/2016 | Ueda et al. |
| 2016/0166824 A1* | 6/2016 | Lev ............... A61M 39/10 604/411 |
| 2016/0199569 A1 | 7/2016 | Yevmenenko et al. |
| 2016/0228644 A1 | 8/2016 | Cabiri |
| 2016/0287475 A1 | 10/2016 | Yevmenenko et al. |
| 2016/0367439 A1 | 12/2016 | Davis et al. |
| 2018/0008513 A1 | 1/2018 | Ibuchi et al. |
| 2018/0161243 A1 | 6/2018 | Ariagno et al. |
| 2018/0221572 A1 | 8/2018 | Schlitt et al. |
| 2018/0303720 A1 | 10/2018 | Kennard et al. |
| 2019/0083357 A1 | 3/2019 | David et al. |
| 2019/0117514 A1 | 4/2019 | Denenburg et al. |
| 2019/0133885 A1 | 5/2019 | Wu et al. |
| 2019/0343725 A1 | 11/2019 | Denenburg |
| 2020/0093692 A1 | 3/2020 | Lev et al. |
| 2020/0276084 A1 | 9/2020 | Denenburg |
| 2020/0282133 A1 | 9/2020 | Mason et al. |
| 2020/0330326 A1 | 10/2020 | Merchant et al. |
| 2020/0376194 A1 | 12/2020 | Fabrikant et al. |

FOREIGN PATENT DOCUMENTS

| | | |
|---|---|---|
| CN | 1747683 A | 3/2006 |
| CN | 1863566 A | 11/2006 |
| CN | 1950049 A | 4/2007 |
| CN | 101001661 A | 7/2007 |
| CN | 101687083 A | 3/2010 |
| CN | 201330626512 | 12/2013 |
| CN | 106413799 A | 2/2017 |
| CN | 306375580 S | 3/2021 |
| DE | 1064693 B | 9/1959 |
| DE | 1913926 A1 | 9/1970 |
| DE | 4122476 A1 | 1/1993 |
| DE | 4314657 A1 | 11/1994 |
| DE | 4408498 A1 | 5/1995 |
| DE | 19504413 A1 | 8/1996 |
| DE | 202004012714 U1 | 11/2004 |
| DE | 102007046951 B3 | 2/2009 |
| DE | 202009011019 U1 | 12/2010 |
| EM | 001126270-0001 | 4/2009 |
| EM | 001680703 | 3/2010 |
| EM | 001680703-0001 | 8/2010 |
| EM | 001680703-0002 | 8/2010 |
| EM | 002446062-0001 | 8/2010 |
| EM | 002446062-0002 | 8/2010 |
| EM | 000627237-0001 | 10/2010 |
| EM | 002446062 | 4/2014 |
| EM | 006630893 | 7/2019 |
| EM | 006630893-0001 | 8/2019 |
| EM | 008039507-0004 | 1/2021 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0426403 A1 | 5/1991 |
| EP | 0282545 B1 | 2/1992 |
| EP | 0518397 A1 | 12/1992 |
| EP | 0521460 A1 | 1/1993 |
| EP | 0582038 A2 | 2/1994 |
| EP | 0598918 A1 | 6/1994 |
| EP | 0637443 A1 | 2/1995 |
| EP | 0737467 A1 | 10/1996 |
| EP | 0761562 A1 | 3/1997 |
| EP | 0765652 A1 | 4/1997 |
| EP | 0765853 A1 | 4/1997 |
| EP | 0806597 A1 | 11/1997 |
| EP | 0814866 A1 | 1/1998 |
| EP | 0829248 A2 | 3/1998 |
| EP | 0830874 A2 * | 3/1998 |
| EP | 0856331 A2 | 8/1998 |
| EP | 0882441 A2 | 12/1998 |
| EP | 0887085 A2 | 12/1998 |
| EP | 0887885 A2 | 12/1998 |
| EP | 0897708 A2 | 2/1999 |
| EP | 0898951 A2 | 3/1999 |
| EP | 0960616 A2 | 12/1999 |
| EP | 1008337 A1 | 6/2000 |
| EP | 1029526 A1 | 8/2000 |
| EP | 1034809 A1 | 9/2000 |
| EP | 1051988 A2 | 11/2000 |
| EP | 1323403 A1 | 7/2003 |
| EP | 1329210 A1 | 7/2003 |
| EP | 1396250 A1 | 3/2004 |
| EP | 1454609 A1 | 9/2004 |
| EP | 1454650 A1 | 9/2004 |
| EP | 1498097 A2 | 1/2005 |
| EP | 1872824 A1 | 1/2008 |
| EP | 1911432 A1 | 4/2008 |
| EP | 1919432 A1 | 5/2008 |
| EP | 1930038 A2 | 6/2008 |
| EP | 2090278 A1 | 8/2009 |
| EP | 2351548 A1 | 8/2011 |
| EP | 2351549 A1 | 8/2011 |
| EP | 2462913 A1 | 6/2012 |
| EP | 2512399 A1 | 10/2012 |
| EP | 2416739 B1 | 6/2016 |
| FR | 2029242 A5 | 10/1970 |
| FR | 2856660 A1 | 12/2004 |
| FR | 2869795 A1 | 11/2005 |

(56) References Cited

FOREIGN PATENT DOCUMENTS

| | | |
|---|---|---|
| FR | 2931363 A1 | 11/2009 |
| GB | 1444210 A | 7/1976 |
| IL | 171662 | 10/2005 |
| IL | 186290 | 1/2008 |
| JP | 03-062426 B2 | 9/1991 |
| JP | 03-205560 A | 9/1991 |
| JP | 04-329954 A | 11/1992 |
| JP | 06-050656 U | 7/1994 |
| JP | 08-000710 A | 1/1996 |
| JP | 09-104460 A | 4/1997 |
| JP | 09-104461 A | 4/1997 |
| JP | 10-118158 A | 5/1998 |
| JP | 10-504736 A | 5/1998 |
| JP | 11-503627 A | 3/1999 |
| JP | 11-319031 A | 11/1999 |
| JP | 2000-508934 A | 7/2000 |
| JP | 2000-237278 A | 9/2000 |
| JP | 2000-262497 A | 9/2000 |
| JP | 2001-505083 A | 4/2001 |
| JP | 2002-035140 A | 2/2002 |
| JP | 2002-516160 A | 6/2002 |
| JP | 2002-355318 A | 12/2002 |
| JP | 2003-033441 A | 2/2003 |
| JP | 2003-102807 A | 4/2003 |
| JP | 2003-513709 A | 4/2003 |
| JP | 2004-501721 A | 1/2004 |
| JP | 2004-097253 A | 4/2004 |
| JP | 2004-522541 A | 7/2004 |
| JP | 2004-267776 A | 9/2004 |
| JP | 2005-270629 A | 10/2005 |
| JP | 2005-537048 A | 12/2005 |
| JP | 2006-061421 A | 3/2006 |
| JP | 2008-220961 A | 9/2008 |
| JP | 2009-513294 A | 4/2009 |
| JP | 4329954 B2 | 9/2009 |
| JP | 2010-063622 A | 3/2010 |
| JP | 2010-179128 A | 8/2010 |
| JP | 2012-205769 A | 10/2012 |
| JP | 2013-520272 A | 6/2013 |
| JP | 2014-000220 A | 1/2014 |
| JP | 2015-211763 A | 11/2015 |
| JP | 2019-015749 A | 1/2019 |
| JP | D201915749 | 7/2019 |
| WO | 86/01487 A1 | 3/1986 |
| WO | 86/01712 A1 | 3/1986 |
| WO | 86/05683 A1 | 10/1986 |
| WO | 90/03536 A1 | 4/1990 |
| WO | 94/03373 A1 | 2/1994 |
| WO | 95/07066 A1 | 3/1995 |
| WO | 95/07720 A1 | 3/1995 |
| WO | 95/13785 A1 | 5/1995 |
| WO | 96/00053 A1 | 1/1996 |
| WO | 96/09083 A1 | 3/1996 |
| WO | 96/29113 A1 | 9/1996 |
| WO | 97/36636 A1 | 10/1997 |
| WO | 98/32411 A1 | 7/1998 |
| WO | WO-9833449 A1 * | 8/1998 ................ A61J 1/10 |
| WO | 98/37854 A1 | 9/1998 |
| WO | 99/61093 A1 | 12/1999 |
| WO | 01/02490 A1 | 1/2001 |
| WO | 01/28490 A1 | 4/2001 |
| WO | 01/30425 A1 | 5/2001 |
| WO | 01/32524 A1 | 5/2001 |
| WO | 01/60311 A1 | 8/2001 |
| WO | 01/89607 A2 | 11/2001 |
| WO | 01/91693 A2 | 12/2001 |
| WO | 02/02165 A2 | 1/2002 |
| WO | 02/09797 A1 | 2/2002 |
| WO | 02/32372 A1 | 4/2002 |
| WO | 02/36191 A2 | 5/2002 |
| WO | 02/66100 A2 | 8/2002 |
| WO | 02/89900 A1 | 11/2002 |
| WO | 03/51423 A2 | 6/2003 |
| WO | 03/70147 A2 | 8/2003 |
| WO | 03/79956 A1 | 10/2003 |
| WO | 03079956 A1 | 10/2003 |
| WO | 2004/004806 A1 | 1/2004 |
| WO | 2004/041148 A1 | 5/2004 |
| WO | 2004/096113 A2 | 11/2004 |
| WO | 2005/002492 A1 | 1/2005 |
| WO | 2005/018703 A2 | 3/2005 |
| WO | 2005/041846 A2 | 5/2005 |
| WO | 2005/105014 A2 | 11/2005 |
| WO | 2005/120431 A1 | 12/2005 |
| WO | 2006/099441 A2 | 9/2006 |
| WO | 2006/124634 A1 | 11/2006 |
| WO | 2007/015233 A1 | 2/2007 |
| WO | 2007/017868 A1 | 2/2007 |
| WO | 2007/052252 A1 | 5/2007 |
| WO | 2007/079305 A2 | 7/2007 |
| WO | 2007/101772 A1 | 9/2007 |
| WO | 2007/105221 A1 | 9/2007 |
| WO | 2007/130809 A2 | 11/2007 |
| WO | 2008/068756 A2 | 6/2008 |
| WO | 2008/076459 A1 | 6/2008 |
| WO | 2008/081424 A2 | 7/2008 |
| WO | 2008/126090 A1 | 10/2008 |
| WO | 2008/135989 A1 | 11/2008 |
| WO | 2009/026443 A2 | 2/2009 |
| WO | 2009/029010 A1 | 3/2009 |
| WO | 2009/038860 A2 | 3/2009 |
| WO | 2009/040804 A2 | 4/2009 |
| WO | 2009/087572 A1 | 7/2009 |
| WO | 2009/093249 A1 | 7/2009 |
| WO | 2009/112489 A1 | 9/2009 |
| WO | 2009/140511 A1 | 11/2009 |
| WO | 2009/146088 A1 | 12/2009 |
| WO | 2010/061743 A1 | 6/2010 |
| WO | 2010/078227 A1 | 7/2010 |
| WO | 2010/117471 A2 | 10/2010 |
| WO | 2010/117580 A1 | 10/2010 |
| WO | 2011/004360 A1 | 1/2011 |
| WO | 2011/024725 A1 | 3/2011 |
| WO | 2011/025719 A1 | 3/2011 |
| WO | 2011/039747 A1 | 4/2011 |
| WO | 2011/058545 A1 | 5/2011 |
| WO | 2011/058548 A1 | 5/2011 |
| WO | 2011/077434 A1 | 6/2011 |
| WO | 2011/090955 A1 | 7/2011 |
| WO | 2011/104711 A1 | 9/2011 |
| WO | 2011/132657 A1 | 10/2011 |
| WO | 2011/150037 A1 | 12/2011 |
| WO | 2011/156373 A1 | 12/2011 |
| WO | 2012/004784 A1 | 1/2012 |
| WO | 2012/004790 A2 | 1/2012 |
| WO | 2012/063230 A1 | 5/2012 |
| WO | 2012/143921 A1 | 10/2012 |
| WO | 2012/150587 A1 | 11/2012 |
| WO | 2013/001525 A1 | 1/2013 |
| WO | 2013/127813 A1 | 9/2013 |
| WO | 2013/134246 A1 | 9/2013 |
| WO | 2013/148435 A1 | 10/2013 |
| WO | 2013/156944 A1 | 10/2013 |
| WO | 2013/156994 A1 | 10/2013 |
| WO | 2014/033706 A2 | 3/2014 |
| WO | 2014/033710 A1 | 3/2014 |
| WO | 2014/099395 A1 | 6/2014 |
| WO | 2014/170888 A1 | 10/2014 |
| WO | 2014/174278 A1 | 10/2014 |
| WO | 2015/009746 A2 | 1/2015 |
| WO | 2015/019343 A1 | 2/2015 |
| WO | 2016/023590 A1 | 2/2016 |
| WO | 2017/203512 A1 | 11/2017 |
| WO | 2018/104930 A1 | 6/2018 |
| WO | 2018/104932 A1 | 6/2018 |
| WO | 2018/178971 A1 | 10/2018 |
| WO | 2020/222220 A1 | 11/2020 |

OTHER PUBLICATIONS

Office Action dated Jun. 15, 2012 in U.S. Appl. No. 29/413,170.
Office Action dated Jun. 21, 2012 in U.S. Appl. No. 12/596,167.

(56) References Cited

OTHER PUBLICATIONS

Office Action dated Jun. 8, 2010 in U.S. Appl. No. 12/112,490 by Zinger.
Office Action dated Mar. 1, 2012 in CN Application No. 200880108283.4.
Office Action dated Mar. 10, 2015 in EP Application No. 12 812 395.7.
Office Action dated Mar. 13, 2012 in CA Application No. 2,563,643.
Office Action dated Mar. 17, 2015 in U.S. Appl. No. 14/504,979 by Lev.
Office Action dated Mar. 25, 2016 in U.S. Appl. No. 29/478,726 by Lev.
Office Action dated Mar. 28, 2016 in JP Application No. 2016-507113.
Office Action dated Mar. 6, 2012 in U.S. Appl. No. 12/678,928.
Office Action dated May 12, 2011 in U.S. Appl. No. 12/063,176.
Office Action dated May 27, 2010 in U.S. Appl. No. 11/559,152.
Office Action dated May 28, 2015 in U.S. Appl. No. 14/391,792 by Lev.
Office Action dated May 31, 2013 in U.S. Appl. No. 13/505,790.
Office Action dated May 6, 2014 in U.S. Appl. No. 13/505,881 by Lev.
Office Action dated Nov. 11, 2013 in IL Application No. 218730.
Office Action dated Nov. 28, 2013 in IN Application No. 4348/DELNP/2008.
Office Action dated Nov. 29, 2010 in U.S. Appl. No. 11/568,421.
Office Action dated Oct. 5, 2005 in U.S. Appl. No. 10/062,796.
Office Action dated Oct. 5, 2015 in U.S. Appl. No. 14/385,212 by Lev.
Office Action dated Oct. 6, 2003 in U.S. Appl. No. 10/062,796.
Office Action dated Oct. 8, 2013 in CN Application No. 201080043825.1.
Office Action dated Sep. 28, 2010 in U.S. Appl. No. 12/112,490 by Zinger.
Office Action issued Jul. 31, 2012 in U.S. Appl. No. 12/598,469.
Office Action issued May 25, 2021 issued in Japanese Application No. 2020-553506.
Overview—Silicone Rubber [retrieved from http://www.knovel.com/web/portal/browse/display?_EXT_KNOVEL_DISPLAY_bookid=1023&Vertica11D=0 on Feb. 9, 2011].
Photographs of Alaris Medical Systems SmartSite.RTM. device, 5 pages, 2002.
Publication dale of Israeli Patent Application 186290 [on-line]. Retrieved from Internet May 24, 2010. URL :<http://www.ilpatsearch.justrice.gov.il/UI/Requestslistaspx>. (1 page).
Smart Site Needle-Free Systems, Alaris Medical Systems Webpage, 4 pages, Feb. 2006.
Smart Site.RTM. Alaris Medical Systems Product Brochure, 4 pages, Issue 1, Oct. 1999.
Summit International Medical Technologies Inc., Vial Direct to Bag Spike 2020.
The MixJect transfer system, as shown in the article, "Advanced Delivery Devices," Drug Delivery Technology Jul./Aug. 2007 vol. 7 No.7 [on-line]. [Retrieved from Internet May 14, 2010.] URL: <http://www.drugdeiverytech-online.com/drugdelivery/200707/?pg=28pg28>. (3 pages).
Translation of Office Action dated Apr. 15, 2013 in JP Application No. 2008-538492.
Translation of Office Action dated Jun. 18, 2012 in JP Application No. 2008-538492.
U.S. Appl. No. 14/005,751 by Denenburg, filed Sep. 17, 2013.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.
U.S. Appl. No. 13/883,289 by Lev, filed May 3, 2013.
U.S. Appl. No. 13/884,981 by Denenburg, filed May 13, 2013.
U.S. Appl. No. 14/345,094 by Lev, filed Mar. 14, 2014.
U.S. Appl. No. 14/366,306 by Lev, filed Jun. 18, 2014.
U.S. Appl. No. 14/385,212 by Lev, filed Sep. 15, 2014.
U.S. Appl. No. 14/391,792 by Lev, filed Oct. 10, 2014.
U.S. Appl. No. 14/423,595 by Lev, filed Feb. 24, 2015.
U.S. Appl. No. 14/423,612 by Lev, filed Feb. 24, 2015.
U.S. Appl. No. 14/425,582 by Lev, filed Mar. 3, 2015.
U.S. Appl. No. 14/504,979 by Lev, filed Oct. 2, 2014.
U.S. Appl. No. 14/784,300 by Lev, filed Oct. 14, 2015.
U.S. Appl. No. 14/888,590 by Marks, filed Nov. 2, 2015.
U.S. Appl. No. 29/438,134 by Lev, filed Nov. 27, 2012.
U.S. Appl. No. 29/438,141 by Gilboa, filed Nov. 27, 2012.
U.S. Appl. No. 29/478,723 by Lev, filed Jan. 8, 2014.
U.S. Appl. No. 29/478,726 by Lev, filed Jan. 8, 2014.
U.S. Appl. No. 29/502,037 by Lev, filed Sep. 11, 2014.
U.S. Appl. No. 29/502,053 by Lev, filed Sep. 11, 2014.
U.S. Appl. No. 29/544,969 by Ben Shalom, filed Nov. 9, 2015.
Vial-Mate Adapter Device, Baxter, May 2017, downloaded from web page:http://www.baxtermedicationdeliveryproducts.com/drug-delivery/vialmate.html, Download Date: Jul. 28, 2017, original posting date: unknown, 1page.
Vial2Bag DC, downloaded from webpage: https://www.youtube.com/watch?v=FEOkg1xNBrs, Original posting date: Aug. 21, 2014, 1 page.
West Vial2Bag DC system, Oct. 2, 2014, https://web.archive.org/web/2014002065133/http://www.westpharma.com/en/products/Pages/Reconstitutionsystems.aspx.
Written Opinion dated Aug. 16, 2012 in Int'l Application No. PCT/IL2012/000164.
Written Opinion dated Jul. 31, 2013 in Int'l Application No. PCT/IL2013/050313.
Written Opinion dated Jun. 5, 2013 in Int'l Application No. PCT/IL2012/050407.
Written Opinion of ISR dated Jun. 19, 2006 in Int'l Application No. PCT/IL2005/000376.
Written Opinion of the Int'l Searching Authority Issued Oct. 27, 2008 in Int'l Application No. PCT/US2008/070024.
Written Opinion of the ISR dated Oct. 17, 2009 in Int'l Application No. PCT/IL08/00517.
Youtube, "ADVCARE—Vial Direct to bag Spoke", first available Oct. 31, 2018 (https://www.youtube.com/watch?v=dd8ctggkrfM&feature=emb_title)(2018).
Youtube, "vial2Bag DC", first available Feb. 1, 2018, (https://www.youtube.com/watch?v=abSKPo5e_Hg) (Year:2018).
Youtube, "Vial2Bag.RTM. Needleless IV Transfer System from Helapet Ltd", first available Aug. 21, 2014 (https://www.youtube.com/watch?v=yFejsvDeemE) (Year: 2014).
Int'l Search Report Issued Jul. 27, 2007 in Int'l Application No. PCT/IL2007/000343.
Int'l Preliminary Report on Patentability dated Aug. 24, 2015 in Int'l Application No. PCT/IL2014/050405.
Int'l Search Report and Written Opinion dated Jul. 21, 2020 in Int'l Application No. PCT/IL2020/050362.
Int'l Search Report and Written Opinion dated Mar. 29, 2019 in Int'l Application No. PCT/IB2018/059577.
Int'l Search Report and Written Opinion issued on May 4, 2011 in Int'l Application No. PCT/IL2010/001077.
Int'l Search Report dated Apr. 24, 2020 in Int'l Application No. PCT/US2020/050020.
Int'l Search Report dated Aug. 25, 2008 in Int'l Application No. PCT/IL2008/000517.
Int'l Search Report dated Jan. 22, 2013 in Int'l Application No. PCT/IL2012/000354.
Int'l Search Report dated Nov. 20, 2006 in Int'l Application No. PCT/IL2006/000881.
International Search Report and Written Opinion dated Oct. 17, 2014 in International Application No. PCT/IL2014/050680.
International Search Report dated Jan. 23, 2007 in Int'l Application No. PCT/IL/2006/001228.
International Search Report dated Mar. 30, 2011 in Int'l Application No. PCT/IL2010/000939.
International Search Report Issued Aug. 28, 2008 in Int'l Application No. PCT/IL2008/000606.
Intl Search Report dated Dec. 6, 2006 in Int'l Application No. PCT/IL2006/000912.

(56) References Cited

OTHER PUBLICATIONS

IV disposables sets catalogue, Cardinal Health, Alaris(Registered) products, SmartSite(Registered) access devices and accessories product No. 10013365, SmartSite add-0n bag access device with spike adapter and needle-free valve bag access port, pp. 1-5, Fall edition (2007).
Merchant "An engineered control device for needle free reconstitution and transfer of compounded sterile intravenous Drug solutions for immediate use to assist in complying with United States Pharmacopeia Chapter <797> standard", Adv Care, 2 pages, 2018.
MixJect, downloaded from webpage: http://www.westpharma.com/en/products/Pages/MixjecLaspx, Download Date: Aug. 8, 2012, 1 page.
MixJet Product Information Sheet, downloaded from webpage: http://www.westpharma.com/SiteCollectionDocuments/Recon/mixject%20product%20sheet.pdf; 1 page.
Non-Vented Vial Access Pin with ULTRASITE.RM. Valve, B. Braun Medical, Inc. website and product description, 3 pages, Feb. 2006.
Notice of Allowance dated Jan. 12, 2016 in U.S. Appl. No. 14/385,212 by Lev.
Notice of Allowance dated Mar. 17, 2016 in U.S. Appl. No. 29/502,037 by Lev.
Novel Transfer, Mixing and Drug Delivery System, MOP Medimop Medical Projects Ltd. Catalog, 4 pages, Rev. 4, 2004.
Office Action dated Apr. 17, 2014 in CN Application No. 201080051201.4.
Office Action dated Apr. 2, 2013 in U.S. Appl. No. 13/505,790.
Office Action dated Apr. 20, 2010 in U.S. Appl. No. 11/997,569.
Office Action dated Apr. 9, 2015 in U.S. Appl. No. 13/883,289 by Lev.
Office Action dated Aug. 20, 2013 in U.S. Appl. No. 13/576,461 by Lev.
Office Action dated Aug. 24, 2015 in U.S. Appl. No. 14/366,306 by Lev.
Office Action dated Aug. 3, 2011 in JP Application No. 2008-525719.
Office Action dated Aug. 7, 2015 in JP Application No. 2015-529206.
Office Action dated Dec. 13, 2010 in U.S. Appl. No. 12/293, 122.
Office Action dated Dec. 20, 2010 in U.S. Appl. No. 12/063, 176.
Office Action dated Dec. 23, 2010 in U.S. Appl. No. 29/334,696.
Office Action dated Dec. 9, 2015 in U.S. Appl. No. 29/478,723 by Lev.
Office Action dated Dec. 9, 2015 in U.S. Appl. No. 29/478,726 by Lev.
Office Action dated Feb. 13, 2014 in U.S. Appl. No. 13/884,981 by Denenburg.
Office Action dated Feb. 20, 2009 in U.S. Appl. No. 11/694,297.
Office Action dated Feb. 22, 2005 in U.S. Appl. No. 10/062,796.
Office Action dated Feb. 7, 2011 in U.S. Appl. No. 12/783,194.
Office Action dated Jan. 17, 2014 in CN Application No. 201180006534.X.
Office Action dated Jan. 2, 2014 in U.S. Appl. No. 13/505,881 by Lev.
Office Action dated Jan. 2, 2015 in U.S. Appl. No. 29/438, 141 by Gilboa.
Office Action dated Jan. 20, 2010 in JP Application No. 2007-510229.
Office Action dated Jan. 23, 2013 in U.S. Appl. No. 12/112,490 by Zinger.
Office Action dated Jan. 5, 2015 in U.S. Appl. No. 29/413,220 by Lev.
Office Action dated Jul. 11, 2011 in U.S. Appl. No. 12/293,122.
Office Action dated Jul. 13, 2012 in U.S. Appl. No. 12/112,490 by Zinger.
Office Action dated Jul. 31, 2014 in U.S. Appl. No. 29/438,141 by Gilboa.
Office Action dated Jun. 1, 2010 in U.S. Appl. No. 11/568,421.
Office Action dated Jun. 14, 2012 in U.S. Appl. No. 29/376,980.
Youtube.com, Vial2Bag DC, Aug. 21, 2014, https://www.youtube.com/watch?v=FEOkglxNBrs.
Int'l Search Report issued Apr. 24, 2020 in Int'l Application No. PCT/US2020/050020.
Article with picture of West Pharmaceutical Services Vial2Bag Needleless System, [on-line; IPIPS Newsletter, Oct. 26, 2007], [retrieved from Internet Feb. 16, 2010]; URL: ,http://www.isips.org/reports/ISIPS_Newsletter_October_26_2007.html.> (7 pages, see pp. 5-6).
Facebook "West Pharmaceutical Services, Inc.", first available Oct. 21, 2014 (https://www.facebook.com/westpharma/photos/710246859056351)(2014).
Article with picture of West Pharmaceutical Services' Vial2Bag Needleless System, [on-line]; ! Sips Newsletter, Oct. 26, 2007; retrieved from Internet Feb. 16, 2010; URL :<http://www.isips.org/reports/ISIPS_Newsletter_October_26_2007.html.> (7 pages, see pp. 5-6).
Decision to Grant dated Apr. 12, 2010 in EP Application No. 08738307.1.
Drug Administration Systems product information sheets; http://www.westpharma.com/eu/en/products/Pages/Vial2Bag.aspx; pp. 1-3 (admitted prior art).
English translation of an Office Action dated Apr. 28, 2014 in JP Application No. 2013-537257.
English translation of an Office Action dated Aug. 28, 2014 in JP Application No. 2013-168885.
English translation of an Office Action dated Dec. 25, 2013 in CN Application No. 201180006530.1.
English translation of an Office Action dated Dec. 4, 2013 in CN Application No. 201080051210.3.
English translation of an Office Action dated Feb. 4, 2014 in JP Application No. 2012-554468.
English translation of an Office Action dated Jan. 9, 2014 in JP Application No. 2010-526421.
English translation of an Office Action dated Jul. 26, 2013 in JP Application No. 2012-538464.
English translation of an Office Action dated Jun. 19, 2013 in JP Application No. 2012-531551.
English translation of an Office Action dated Jun. 30, 2014 in CN Application No. 201180052962.6.
English translation of an Office Action dated Sep. 10, 2013 in JP Application No. 2012-554468.
Extended European Search Report dated Jun. 3, 2014 in EP Application No. 08781828.2.
Grifols Vial Adapter Product Literature, 2 pages, Jan. 2002.
http://www.westpharma.com/en/products/Pages/Mixject.aspx (admitted prior art), [Retrieved on Aug. 8, 2012].
Int'l Preliminary Report on Patenability Issued Oct. 20, 2009 in Int'l Application No. PCT/IL2008/000517.
Int'l Preliminary Report on Patentability issued Jan. 14, 2014 in Int'l Application No. PCT/IL2012/050516.
Int'l Preliminary Report on Patentability issued May 6, 2008 in Int'l Application No. PCT/IL2006/001228.
Int'l Preliminary Report on Patentability issued May 12, 2014 in Int'l Application No. PCT/IL2013/050316.
Int'l Preliminary Report on Patentability issued Aug. 20, 2014 in Int'l Application No. PCT/IL2012/050407.
Int'l Preliminary Report on Patentability issued Aug. 28, 2012 in Int'l Application No. PCT/IL2011/000186.
Int'l Preliminary Report on Patentability issued Sep. 24, 2013 in Int'l Application No. PCT/IL2012/000354.
Int'l Preliminary Report on Patentability Issued Dec. 4, 2007 in Int'l Application No. PCT/IL2006/000912.
Int'l Preliminary Report on Patentability Issued Jun. 19, 2006 in Int'l Application No. PCT/IL2005/000376.
Int'l Preliminary Report on Patentability Issued Jun. 19, 2008 in Int'l Application No. PCT/IL2007/000343.
Int'l Search Report & Written Opinion issued on Mar. 7, 2012 in Int'l Application No. PCT/IL2011/000829.
Int'l Search Report and Written Opinion issued Mar. 6, 2012 in Int'l Application No. PCT/IL2011/000834.
Int'l Search Report and Written Opinion issued May 8, 2014 in Int'l Application No. PCT/IL2013/050706.

(56) References Cited

OTHER PUBLICATIONS

Int'l Search Report and Written Opinion issued Jul. 16, 2014 in Int'l Application No. PCT/IL2014/050327.
Int'l Search Report and Written Opinion issued Sep. 2, 2014 in Int'l Application No. PCT/IL2014/050405.
Int'l Search Report and Written Opinion issued Mar. 23, 2020 in Int'l Application No. PCT/IL2020/050048.
Int'l Search Report issued Feb. 3, 2011 in Int'l Application No. PCT/IL2010/000777; Written Opinion.
Int'l Search Report issued Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
Int'l Search Report issued Mar. 18, 2013 in Int'l Application No. PCT/IL2012/050516.
Int'l Search Report issued Jun. 5, 2013 in Int'l Application No. PCT/IL2012/050407.
Int'l Search Report issued Jun. 19, 2013 in Int'l Application No. PCT/IL2013/050167.
Int'l Search Report issued Jul. 1, 2013 in Int'l Application No. PCT/IL2013/050180.
Int'l Search Report issued Jul. 26, 2013 in Int'l Application No. PCT/IL2013/050316.
Int'l Search Report issued Jul. 31, 2013 in Int'l Application No. PCT/IL2013/050313.
Int'l Search Report issued Aug. 16, 2012 in Int'l Application No. PCT/IL2012/000164.
Int'l Search Report Issued Oct. 17, 2005 in Int'l Application No. PCT/IL2005/000376.
Int'l Search Report issued Oct. 17, 2011 in Int'l Application No. PCT/IL2011/000511.
Int'l Search Report issued Nov. 25, 2010 in Int'l Application No. PCT/IL2010/000530.
Int'l Search Report Issued Mar. 12, 2009 in Int'l Application No. PCT/IL2008/001278.
Int'l Search Report Issued Mar. 27, 2009 in Int'l Application No. PCT/US2008/070024.
Int'l Search Report issued Jul. 12, 2011 in Int'l Application No. PCT/IL2011/000186.
Int'l Search Report issued Jul. 12, 2011 in Int'l Application No. PCT/IL2011/000187.
Author unknown, Progressive Medical inc. is proud to announce the launch of West's Vial2Bag Agvanced, Progressive Medinc ., [Post Date Oct. 23, 2020], [Site seen Jan. 25, 2022], Seen at URL: https://www.progressivemedinc.com/west-launches-vial2bag-advanced-20mm-admixture-device/ (Year: 2020).
Our Vial2Bag Advanced™ 20mm admixture device , West Pharma, WestPharma @twitter, [Postdate Mar. 19, 2021], [Siteseen Jan. 25, 2022], Seen at URL: https://twitter.com/westpharma/status/1372921057766739971 (Year: 2021).
Vial2Bag Advanced™ 20mm Admixture , West Pharmaceutical Services Inc, Youtube, [post date Nov. 5, 2020], [Site seen Jan. 25, 2022], Seen at URL: https://www.youtube.com/watch?v=J0Am3mt5vn8 (Year: 2020).

* cited by examiner

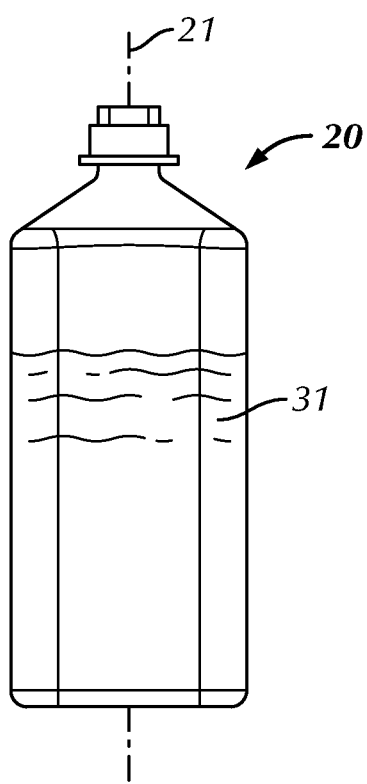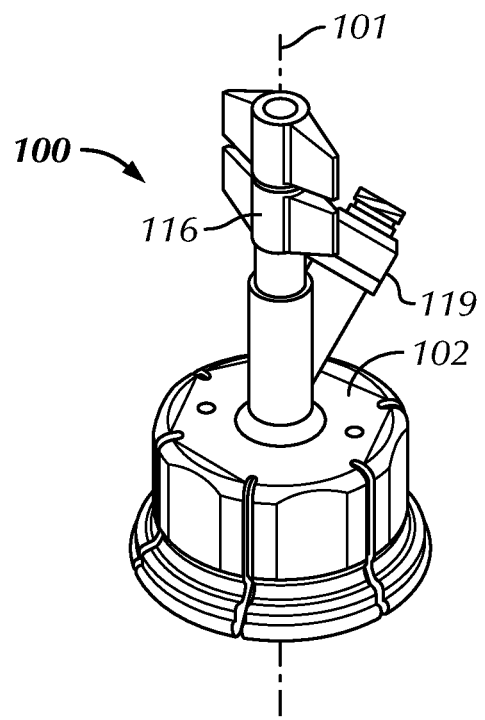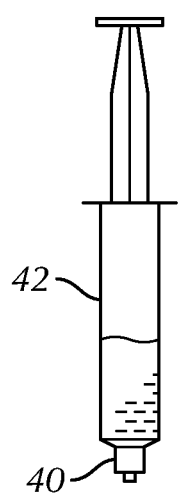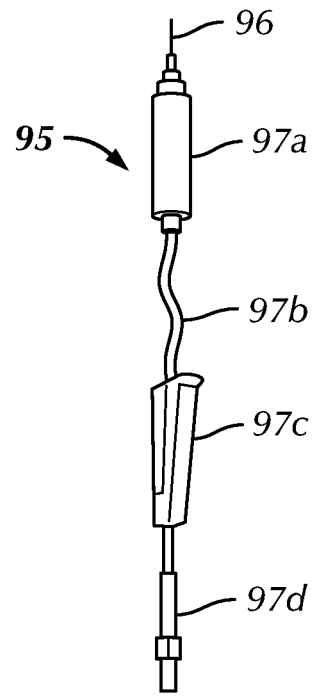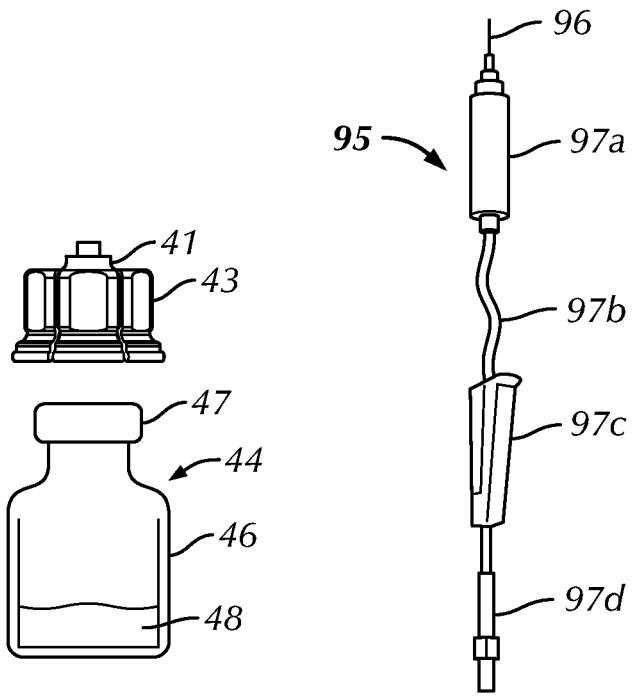
FIG. 1A  FIG. 1B
FIG. 1C  FIG. 1D  FIG. 1E

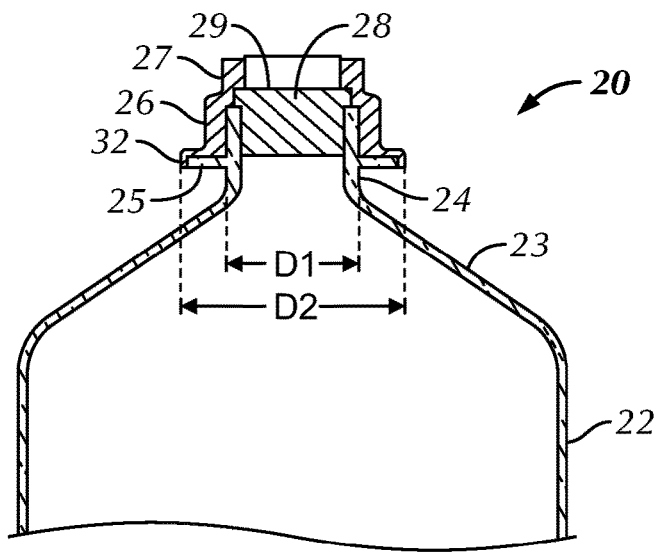
FIG. 2
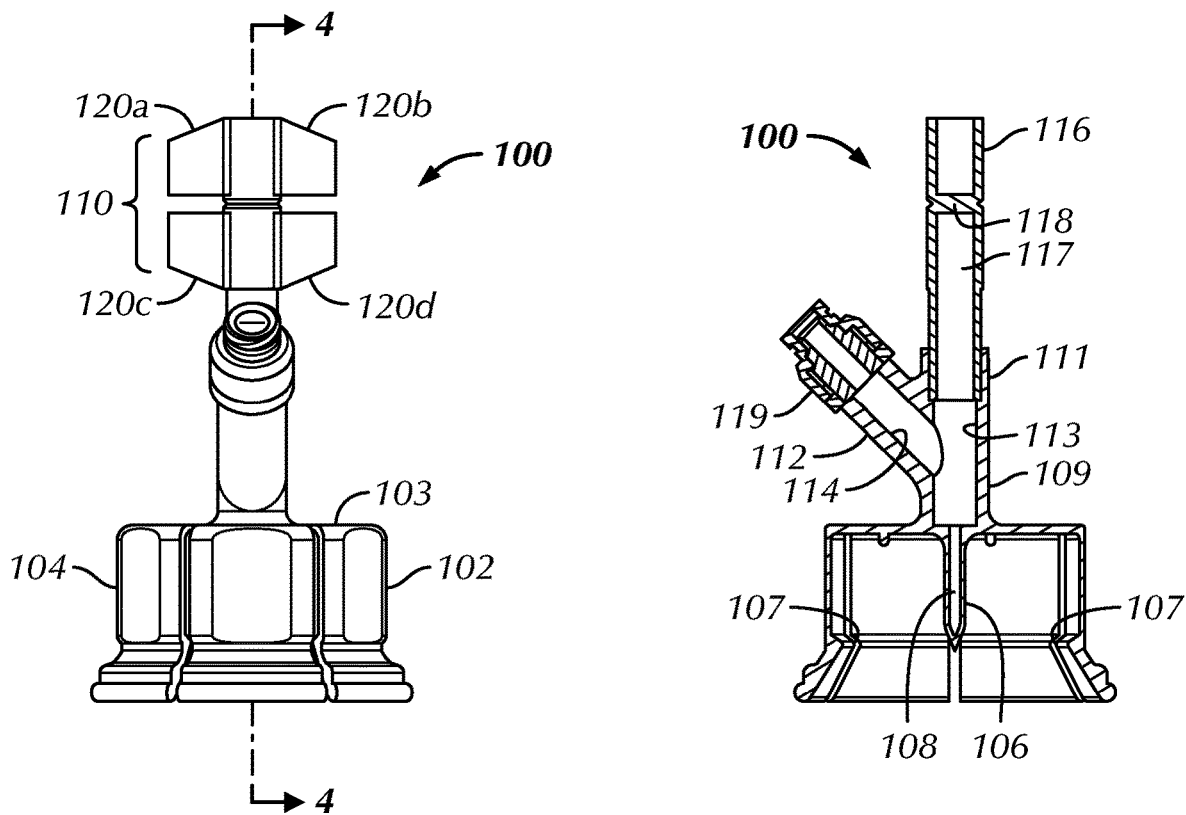
FIG. 3
FIG. 4

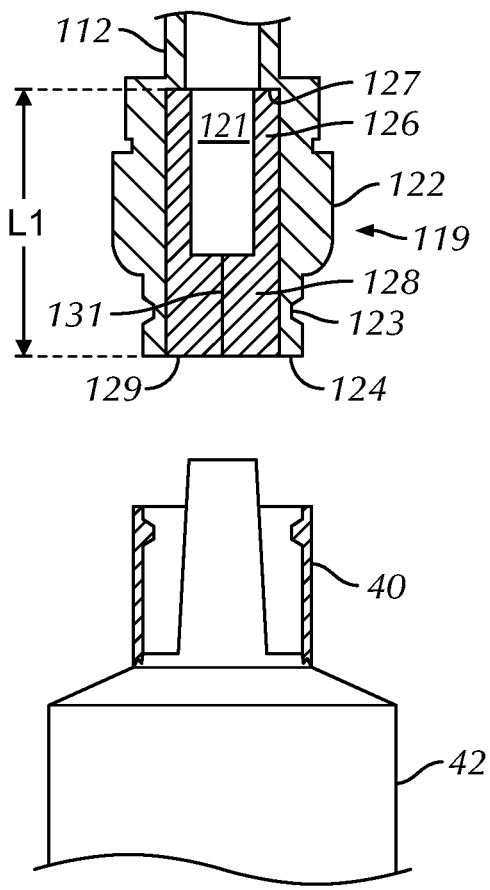
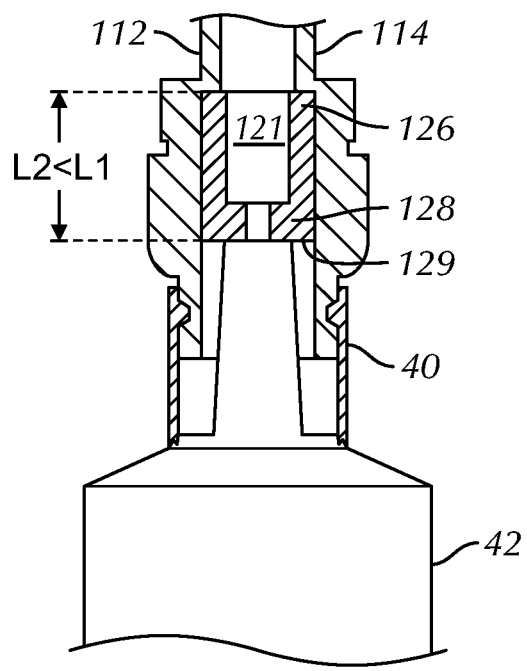
FIG. 5A    FIG. 5B
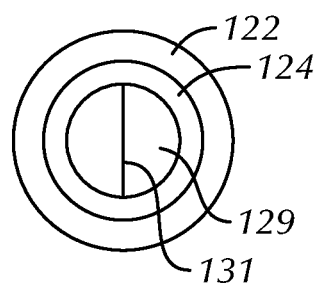
FIG. 6

LIQUID TRANSFER DEVICES FOR USE WITH INTRAVENOUS (IV) BOTTLES

CROSS REFERENCE TO RELATED APPLICATION

This application is a Section 371 of International Application No. PCT/IL2020/050020, filed Jan. 7, 2020, which was published on Jul. 23, 2020, under Publication No. WO 2020/148748 A1, and which claims the benefit of and priority to U.S. Provisional Application No. 62/794,019, filed on Jan. 18, 2019, the contents of which are hereby incorporated by reference in their entirety.

BACKGROUND OF THE INVENTION

The invention relates to liquid transfer devices for use with intravenous (IV) bottles.

Conventional infusion liquid containers containing an infusion liquid to be delivered to a patient take the form of an intravenous (IV) bag or an intravenous (IV) bottle. Some IV bottles are formed from collapsible plastic material such that they collapse similar to an IV bag on administration of their contents to a patient. Other IV bottles are formed from non-collapsible material, for example, rigid plastic, glass, etc. such that they do not collapse on administration of their contents to a patient. Infusion liquid containers are intended to be used with a syringe with a needle for adding a liquid drug to infusion liquid contents to form medicated infusion liquid contents and an infusion set including an IV spike for infusion of medicated infusion liquid contents to a patient.

There is a need for liquid transfer devices for use with IV bottles.

BRIEF SUMMARY OF THE INVENTION

The present invention is directed toward liquid transfer devices for use with intravenous (IV) bottles for infusion of medicated infusion liquid contents to a patient. The liquid transfer devices include a vial adapter for telescopic snap fit mounting on an IV bottle, an initially sealed IV port for sealingly receiving an infusion set's IV spike and a needleless swabable self-sealing port with a female connector for use with a needleless transfer device with a male connector for adding a liquid drug to an IV bottle's infusion liquid contents. The vial adapter includes a puncturing cannula for puncturing an IV bottle stopper on telescopic snap fit mounting on an IV bottle. The needleless swabable self-sealing port affords convenient adding of additives to an IV bottle's infusion liquid contents to form medicated infusion liquid contents. Such adding can either be by way of a vial adapter with a vial or a syringe. A syringe can also be employed for aspirating one or more medicated infusion liquid dosages for administration to a patient prior to infusion of remaining medicated infusion liquid contents. In the case of intended use with a non-collapsible IV bottle, a liquid transfer device includes a venting arrangement for venting during infusion of its medicated infusion liquid contents. The venting arrangement can be implemented as a separate vent port or integral with a vial adapter as a vented vial adapter. A liquid transfer device with a venting arrangement can also be used with a collapsible IV bottle in which case the collapsible IV bottle does not collapse.

Thus, according to one aspect of the present invention a liquid transfer device is provided for use with an intravenous (IV) bottle, an additive transfer device and an infusion set with an IV spike for intravenous administration of infusion liquid to a patient. The IV bottle includes a closed end IV bottle container containing an infusion liquid and tapering towards an open IV bottle neck, an IV bottle crown mounted on the IV bottle neck, and an IV bottle stopper for sealing the IV bottle. The additive transfer device has a male connector. The liquid transfer device has a longitudinal liquid transfer device centerline and comprises:
  a) a vial adapter having a transverse vial adapter top surface and a downward depending vial adapter skirt configured to telescopically mount on the IV bottle crown, the vial adapter having a cannula configured to puncture the IV bottle stopper for fluid communication with the IV bottle container upon mounting on the IV bottle crown,
    the transverse vial adapter top surface having an upright nipple oppositely directed with respect to said cannula,
    the nipple having a first nipple section with a first nipple section lumen in fluid communication with a lumen of the cannula, and
    the nipple having a second nipple section with a second nipple section lumen in fluid communication with the lumen of the cannula;
  b) an IV port extending from the first nipple section and including a sealing membrane comprising a material puncturable by the IV spike of the infusion set; and
  c) a needleless self-sealing port extending from the second nipple section, the needleless self-sealing port configured to couple with the male connector of the additive transfer device.

According to another aspect of the present invention, a method of preparing a medication for intravenous administration of infusion liquid to a patient using a liquid transfer device, an intravenous (IV) bottle, an additive transfer device and an infusion set with an IV spike is provided. As previously noted, the IV bottle includes a closed end IV bottle container containing infusion liquid and tapering towards an open IV bottle neck, an IV bottle crown mounted on the IV bottle neck, and an IV bottle stopper for sealing the IV bottle, and the additive transfer device has a male connector. The method comprises the steps of coupling the male connector of the additive transfer device to a self-sealing port of the liquid transfer device, telescopically mounting a vial adapter of the liquid transfer device onto the crown of the IV bottle and puncturing the IV bottle stopper with a cannula of the liquid transfer device, mixing an additive contained in the additive transfer device with the infusion liquid, and puncturing a sealing membrane of a liquid transfer device with the IV spike of the infusion set.

These and other aspects of the present invention will be apparent in view of the following description.

BRIEF DESCRIPTION OF THE DRAWINGS

The following description of embodiments of the invention will be better understood when read in conjunction with the appended drawings. The drawings are not necessarily drawn to scale. The figures depict one or more implementations in accord with the present concepts, by way of example only, not by way of limitations. In the figures, like reference numerals refer to the same or similar elements. In the drawings:

FIGS. 1A to 1E shows an administration set including a collapsible IV bottle, a liquid transfer device in accordance with a first embodiment of the present invention, a pre-filled needleless syringe, a male vial adapter, a vial and an infusion set;

FIG. 2 is a cross-sectional side view of a top part of FIG. 1's IV bottle along a longitudinal centerline;

FIG. 3 is a front elevational view of FIG. 1's liquid transfer device;

FIG. 4 is a longitudinal cross-sectional side view of the liquid transfer device along line 4-4 in FIG. 3;

FIG. 5A is a cross-sectional side view of the self-sealing access valve of the liquid transfer device in its closed condition and a cross-sectional side view of the tip portion of the pre-filled needleless syringe in a disconnected condition in FIG. 4;

FIG. 5B is a cross-sectional side view of the self-sealing access valve of the liquid transfer device in its open condition and the tip portion of the pre-filled needleless syringe in a connected condition in FIG. 4;

FIG. 6 is a top plan view of the self-sealing access valve of the liquid transfer device in its closed condition;

DESCRIPTION OF THE INVENTION

Figure 7:
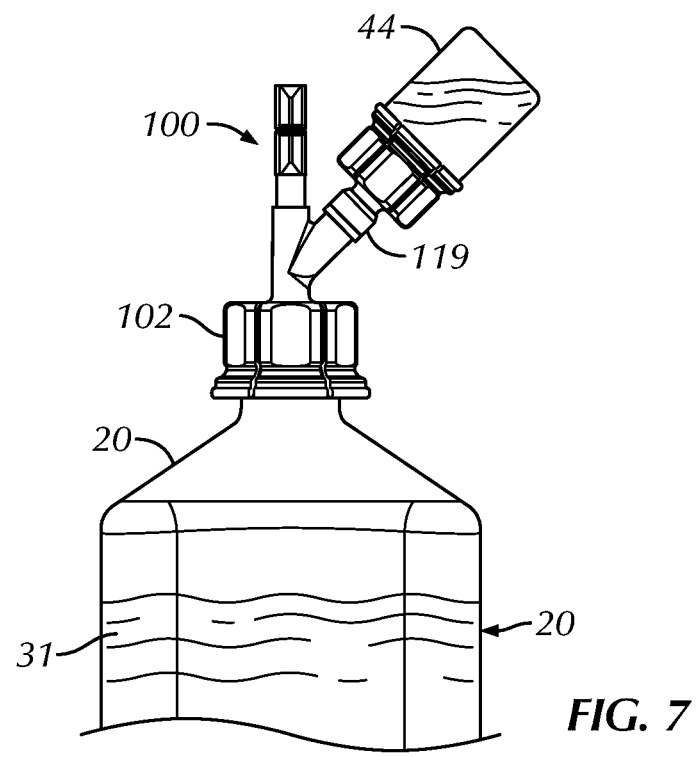
FIG. 7 is a front elevational view showing a section of the collapsible IV bottle, male vial adapter, and vial connected to the liquid transfer device for adding additive from a vial to an IV bottle for forming medicated infusion liquid.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the liquid transfer device and/or IV bottle, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, FIGS. 1A to 1E show various components of an administration set including an intravenous (IV) bottle 20, an additive transfer device, such as a needleless syringe 42 or vial adapter 43, an infusion set 95, and a liquid transfer device 100 in accordance with a first embodiment of the present invention.

FIG. 1A and FIG. 2 show the IV bottle 20 having a longitudinal IV bottle centerline 21 and includes a top end 22 having an IV bottle shoulder 23 tapering to an open narrow diameter IV bottle neck 24 having a diameter D1 and a circumferential collar 25 around the neck 24. The IV bottle 20 includes an IV bottle crown 26 mounted on the IV bottle neck 24. The IV bottle crown 26 includes an IV bottle stopper housing 27 for housing an IV bottle stopper 28 for sealing the IV bottle 20. The stopper housing 27 may include an aperture in order to expose the top surface 29 of the IV bottle stopper 28 for enabling access to the infusion liquid 31 contained by the IV bottle 20. Alternatively, the stopper housing 27 may include a removable portion, such as a pull tab attached to a frangible section of the top of the crown 26, that may be removed to expose the top surface 29 of the IV bottle stopper 28. The IV bottle crown 26 includes a lowermost circular flange 32 spaced apart from the IV bottle shoulder 23 and having a diameter D2, where D2>D1. The circumferential collar 25 around the neck 24 of the IV bottle 20 may serve as a stop for the crown 26 when the crown is mounted over the stopper 28. The IV bottle 20 is made, for example, from a collapsible plastic material configured to collapse in a similar manner as an IV bag to facilitate infusion of medication from an additive transfer device to provide a medicated infusion liquid. IV bottles 20 included in administration sets according to various embodiments of the present invention may be configured to contain various volumes and crown diameters. In a preferred embodiment, the IV bottle crown may have a diameter of about 20 mm or about 32 mm.

As previously mentioned, the additive transfer device may be provided in the form of a syringe or vial adapter, for example. Referring to FIG. 1C, in one embodiment of the present invention, the additive transfer device may be provided in the form of a needleless syringe 42 containing a medicament or other material for infusion and having a tip configured as a male Luer lock connector 41, but the disclosure is not so limited. In an alternative embodiment of the present invention, the additive transfer device may take the form of a vial adapter 43 as illustrated in FIG. 1D for telescopic snap fit mounting onto a vial 44, and the like. The vial 44 includes a vial bottle 46 sealed by a vial stopper 47. The vial 44 contains vial contents 48 that may be in the form of a highly concentrated medicament liquid additive or a lyophilized powder drug requiring reconstitution prior to administration, for example. The syringe 42 may contain similar contents. According to one method of using an embodiment of the invention, the vial contents 48 may be introduced into the IV bottle 20 for mixing with the infusion liquid to form medicated infusion liquid contents for administration to a patient, as will be described in greater detail below.

Referring now to FIG. 1E, the various embodiments of the present invention may include an infusion set 95. The infusion set 95 may comprise an IV spike 96 extending from a first end of a drip chamber 97a. The opposing end of the drip chamber 97a may be connected to a first end of a roller clamp 97c via a length of tubing 97b. A connector 97d may be attached to a second opposing end of the roller clamp 97c. The connector 97d may be provided in the form of a male Luer connector, for example. The IV spike of the infusion set may be provided in a variety of diameters. Preferably, the IV spike has a diameter of approximately 6 mm. Similarly, the tubing 97b may be provided in a variety of diameters and lengths. The length of the tubing is preferably long enough to extend between the end of the liquid transfer device and the patient receiving the medicated infusion liquid with sufficient slack to avoid any patient discomfort. In a preferred embodiment, the tubing may have a diameter of about 2 mm to about 5 mm, more preferably a diameter of approximately 4.1 mm, and a length of about 0.5 m to about 1.5 m.

In FIG. 3 and FIG. 4 a liquid transfer device 100 according to a first embodiment of the present invention is illustrated. The liquid transfer device 100 has a longitudinal liquid transfer device centerline 101 and may be provided as a trifurcated connector body defining an IV port 116 at a first end thereof, a vial adapter 102 at an opposing second end thereof, and a needleless swabable self-sealing port 119 angularly bifurcating from, i.e., branching off of the connector body. In a preferred embodiment, the angle between the needleless swabable self-sealing port 119 and the IV port 116 is an acute angle.

The vial adapter 102 of the liquid transfer device 100 is similar to the previously mentioned vial adapter 43 and may be constructed from a suitable polymeric or plastic material, such as, for example, polycarbonate and the like. In one configuration, the vial adapter 102 may be integrally formed at the second end of the connector body, such that the connector body is of unitary construction, or otherwise permanently secured and sealed to the second end of the trifurcated connector body, for example. As used herein through the specification and the claims, "permanently secured" means not disconnectable/removable without causing damage to the device or portion thereof. As one non-limiting example, the vial adapter 102 may be ultrasonically welded to the second end of the trifurcated connector body.

The vial adapter 102 includes a vial adapter top portion 103 that is transverse to the longitudinal centerline 101 and a vial adapter skirt 104 downwardly depending from the top portion 103. The vial adapter skirt 104 may be made of a rigid, resilient material and include a plurality of longitudinally extending slits to facilitate deflection of the skirt 104 during use, and the depth of the skirt 104 is preferably configured, such that the skirt 104 is capable of being telescopically snap fit over the crown 26 of the IV bottle 20. The vial adapter 102 further includes a puncturing cannula 106 extending away from the underside of the transverse vial adapter top portion 103. The cannula 106 preferably extends along the longitudinal centerline 101 of the liquid transfer device 100 and has a tip for puncturing the IV bottle stopper 28 upon telescopically snap fit mounting the vial adapter 102 on the IV bottle crown 26. The vial adapter skirt 104, similar to the vial adapter 43 of the additive transfer device, may be made of a rigid, resilient material and have a plurality of longitudinally extending slits, as well as at least two inwardly directed protrusions 107 for snap fitting under the flange 32 of the IV bottle crown 26. The puncturing cannula 106 includes at least one internal lumen 108 extending, preferably along the longitudinal centerline 101 of the liquid transfer device 100. A vent in the tip of the cannula 106 provides an open end of the lumen 108.

The cannula 106 of the vial adapter 102 is preferably longer than the height of the stopper 28 of the IV bottle 20. More preferably, the cannula 106 has a length that is substantially similar to the height of the stopper 28, such that when the cannula 106 is inserted into the stopper 28, only the tip portion of the cannula 106 is exposed; thereby, providing a fluid outlet for the liquid contents of the IV bottle 20 and minimizing any dead space volume of liquid when the IV bottle 20 is inverted. The cannula 106 may also be provided with a variety of diameters. In a preferred embodiment, the puncturing cannula 106 has an approximately 3 mm external diameter. The diameter and sharpness of the tip of the puncturing cannula 106 is preferably selected to require as little force as necessary to puncture and insert the cannula 106 into the IV bottle stopper 28, as well as reduce the potential for tearing of the IV bottle stopper 28 that may cause leaking through the stopper 28 around the cannula 106 when the IV bottle 20 is inverted.

The vial adapter 102 may further comprise a Y-shaped nipple 109 extending from an opposing side of the top portion 103 of the vial adapter 102 relative to the puncturing cannula 106. The Y-shaped nipple 109 forms the trifurcated body of the liquid transfer device 100 and includes a first nipple section 111 co-directional with the longitudinal liquid transfer device centerline 101 and a second nipple section 112 angled thereto from which the needleless swabable self-sealing port 119 extends. The first nipple section 111 includes a first nipple section lumen 113 and the second nipple section 112 includes a second nipple section lumen 114. Both nipple section lumens 113 and 114 are in continuous flow communication with the puncturing cannula lumen 108.

The IV port 116 of the liquid transfer device 100 may be integrally formed with or permanently secured within the first nipple section 111 of the Y-shaped nipple 109 and include an internal lumen 117, preferably extending along the longitudinal centerline 101, and a twist off port section 110. The twist off port section 110 may include a removable portion having two opposing tabs 120a, 120b, and a fixed portion also having two opposing tabs 120c, 120d. The tabs facilitate twisting of the top removable portion relative to the bottom fixed portion. Removal of the top portion will expose a sealing membrane 118. The circumferential area around the sealing membrane 118 may be optionally frangible or scored to facilitate removal of the top removable portion of the twist off port section 110. Therefore, the removable portion of the twist off port section 110 may be removed without leading to flow communication beyond the sealing membrane 118. Flow communication beyond the sealing membrane 118, i.e., with the internal lumen 117 and beyond, is only achieved upon puncturing the sealing membrane 118 (as described in further detail below). The twist off port section 110 preferably keeps the IV port 116, and particularly the sealing membrane 118, sterile until use. The IV port 116 may be constructed from suitable flexible plastic material, for example, PVC, and the like, that will allow insertion of the infusion set's IV spike 96 through the sealing membrane 118 in order to provide a fluid connection between the liquid transfer device 100 and the infusion set 95.

The normally closed (NC) needleless swabable self-sealing port 119 mounted in the second nipple section 112, best shown in FIGS. 5A, 5B and 6, may be removably attached or permanently secured to the third end of the trifurcated connector body. The needleless swabable self-sealing port 119 may comprise an internal lumen 121 having one end fitted with a self-sealing access valve 122 for receiving, preferably threadingly receiving, a male connector (e.g., male Luer lock connector 40 of the syringe 42 or male Luer lock connector 41 of the vial adapter 43). The access valve 122 preferably includes corresponding threads 123 on an exterior circumferential surface of an abutment portion 124. Inserted within lumen 121 and access valve portion 122 of the self-sealing port 119 is a compressible plug. The plug is preferably made from an elastomeric material, such as silicone, and includes a main portion 128 having an entry portion surface 129 and a rim portion 126 having a skirt-like configuration and extending from an opposing end of the main portion 128 relative to the entry portion surface 129. The rim portion 126 of the plug is seated against a stop 127 that is preferably configured as a circumferential step or ridge on the inner surface of the access valve 122. The entry portion surface 129 includes a slit 131 formed along at least a portion of a diameter of the entry portion surface 129. The compressible plug within the access valve portion 122 has a length L1 in a relaxed state and is so dimensioned that the entry portion surface 129 is flush with the leading surface of the abutment portion 124 thereby enabling the entry portion surface 129 to be readily swabbed for sterilization purposes (see FIG. 5A). A male connector, such as the male Luer lock connector 40 of the syringe 42 may be screwed onto the corresponding threads 123 on the abutment portion 124 and advanced. During its advancement, the male Luer lock connector 41 compresses the plug to a compressed length L2, which is less than L1. Compression of the plug causes the slit 131 to expand enabling fluid communication between the syringe 42 and the lumen 121 (see FIG. 5B).

Figure 9:
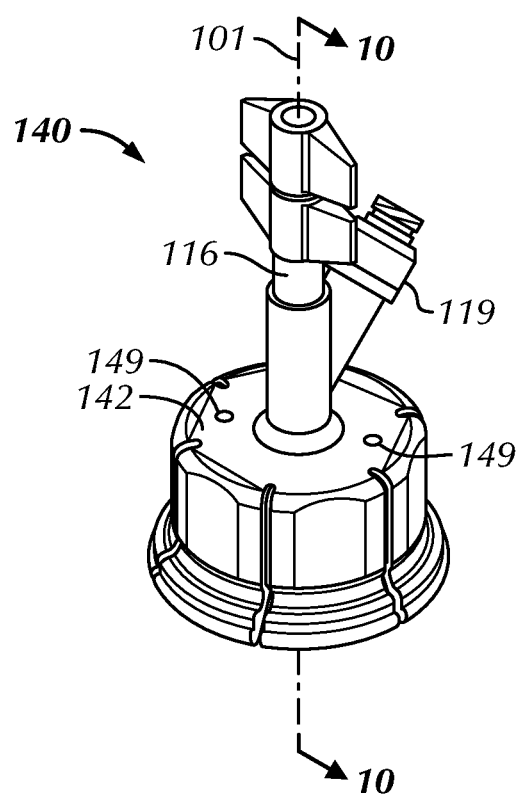
FIG. 9 is a top elevational view of a liquid transfer device with a vented vial adapter in accordance with a second embodiment of the present invention.
Figure 10:
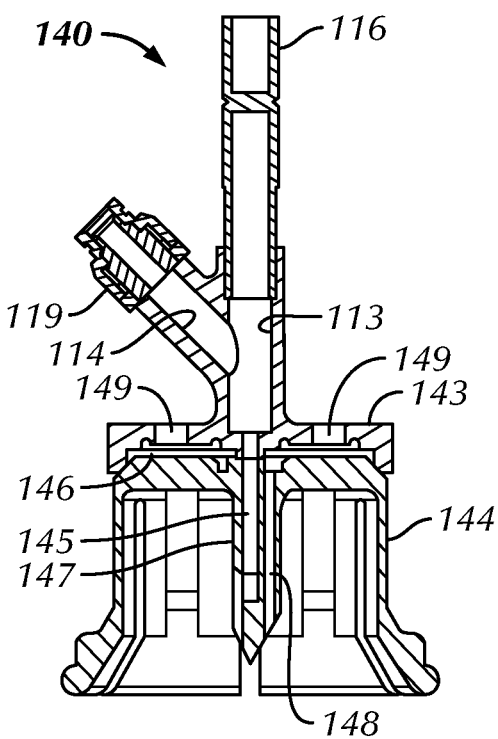
FIG. 10 is a longitudinal cross-sectional side view of the liquid transfer device of FIG. 9 along line 10-10.

An alternative liquid transfer device 140 according to another embodiment of the present invention is provided in FIGS. 9 and 10. Many of the features of the second embodiment of the liquid transfer device 140 are similar to the previously described liquid transfer device 100 and therefore similar parts are likewise numbered. The liquid transfer device 140 is intended to be used with an IV bottle made from rigid material, for example, rigid plastic, glass, etc. which does not collapse on administration of infusion liquid contents therefrom. Accordingly, the liquid transfer device 140 includes a vial adapter 142 similar to the vial adapter 102, except that the vial adapter 142 includes a vial adapter 142 capable of venting an IV bottle during infusion of its medicated infusion liquid contents. The vented vial adapter 142 includes a vial adapter top portion 143 that is transverse to the longitudinal centerline 101 of the liquid transfer device 140. A vial adapter skirt 144 downwardly depends from the vial adapter top portion 143. The vial adapter top portion 143 comprises an internal chamber that also extends in a plane transverse to the longitudinal centerline 101, and an air filter 146 is located within the internal chamber of the vial adapter top portion 143. The vented vial adapter 142 further comprises a dual lumen puncturing cannula 147 having a puncturing cannula vent lumen 148 fluidly connected to the internal chamber containing the air filter 146, and a puncturing cannula liquid lumen 145 in fluid communication with the nipple section lumens 113 and 114 of the liquid transfer device 140. The top surface of the top portion 143 is provided with at least one vent, preferably a plurality of vents 149, that enable fluid communication between the vent lumen 148 and chamber containing the air filter 146 with the external atmosphere.

The vented vial adapter 142 facilitates draining of the liquid contents of the IV bottle through the liquid transfer device 140 when the liquid transfer device 140 is attached to the IV bottle and the IV bottle is inverted. For example after telescopically mounting the vented vial adapter 142 onto the crown of the IV bottle, such that the dual lumen cannula 147 punctures the stopper within the crown and upon inverting the IV bottle, the air from the external environment may be drawn into the vents 149, through the vent lumen 148 and into the IV bottle while the liquid contents drain out of the IV bottle through the liquid lumen 145 and into the first nipple section lumen 113 and/or second nipple section lumen 114.

Figure 8:
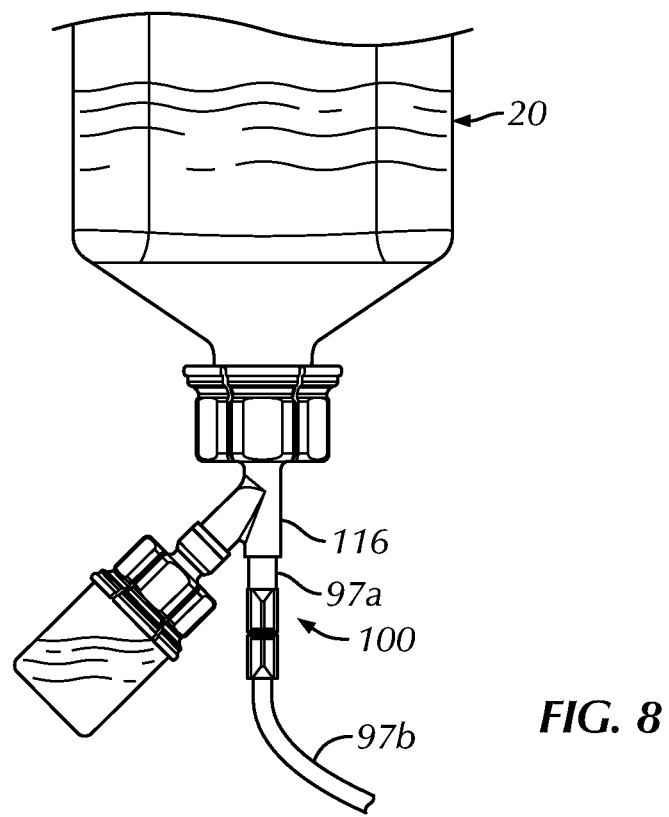
FIG. 8 is a front elevational view showing a section of the collapsible IV bottle, male vial adapter, vial and the IV spike of an infusion set connected to the liquid transfer device for administering medicated infusion liquid to a patient.

Referring now to FIGS. 7 and 8, a method of adding additive to an IV bottle's infusion liquid contents via the liquid transfer device to form medicated infusion liquid according to another embodiment of the present invention is provided. For example, in a first step of one method according to an embodiment of the invention, a vial adapter 43 having a cannula with an internal lumen may be telescopically mounted onto a vial 44 containing a highly concentrated medicament liquid or a solid medicament requiring reconstitution, such that the cannula pierces the stopper 47 of the vial 44 and the vial adapter 43 and vial 44 form a snap fit. The vial adapter 43 may then be connected to the needleless swabable self-sealing port 119 of the liquid transfer device 100. In another embodiment, the tip of a syringe 42 containing liquid or solid contents may be connected to the needleless swabable self-sealing port 119.

In a subsequent step, the vial adapter 102 of the liquid transfer device 100 is telescopically mounted onto the IV bottle crown 26 to form a snap fit between the vial adapter 102 and crown 26. The telescopic mounting of the vial adapter 102 also causes the cannula 106 to puncture the IV bottle stopper 28 for flow communication between the vial 44 and the IV bottle 20. When a vial 44 is attached to the liquid transfer device 100, a user may mix/combine the contents within the vial 44 with the contents within the IV bottle 20 by collapsing the IV bottle to expel liquid 31 from the IV bottle 20 and into the vial 44. Mixing may also be facilitated by optionally positioning the additive transfer device, so that the contents of the additive transfer device drain into the IV bottle 20 under the force of gravity. If the vial 44 contains a solid requiring reconstitution, such as a lyophilized powder drug, the drug can be reconstituted in a similar fashion and then optionally inverted, as previously described, to drain the reconstituted contents of the vial 44 into the IV bottle 20. When a syringe 42 is attached to the liquid transfer device 100, collapsing of the IV bottle 20 is not necessary because the contents of the syringe 42 may be expelled and transferred to the liquid 31 within the IV bottle 20 by depressing the plunger of the syringe 42.

After adding the additive from the additive transfer device to the IV bottle 20, the additive transfer device may be optionally disconnected to re-seal the self-sealing port 119. Alternatively, a syringe may be attached to the self-sealing port 119 and used to aspirate one or more medicated infusion liquid content dosages from the IV bottle 20 for injection to a patient.

Finally, the IV bottle 20 containing the infusion liquid and the liquid transfer device 100 attached thereto are inverted, as illustrated in FIG. 8, the removable portion of the twist off port section 110 is removed to expose the sealing membrane 118, and the IV spike 96 of an infusion set 95 is sealingly inserted into the sealing membrane. The infusion liquid contents 31 of the IV bottle 20 is then ready for administration to a patient via the infusion set 95 in a manner well understood by those of ordinary skill in the art.

It will be appreciated by those skilled in the art that changes could be made to the embodiments described above without departing from the broad inventive concepts thereof. It is understood, therefore, that this invention is not limited to the particular embodiments disclosed, but it is intended to cover modifications within the spirit and scope of the present invention.

I claim:

1. A liquid transfer device for use with an intravenous (IV) bottle, an additive transfer device, and an infusion set with an IV spike for intravenous administration of infusion liquid to a patient, the IV bottle containing an infusion liquid and having a closed end tapering towards an open IV bottle neck, an IV bottle crown mounted on the IV bottle neck, and an IV bottle stopper for sealing the IV bottle, the additive transfer device having a male connector, and the liquid transfer device having a longitudinal centerline and comprising:

a vial adapter having:
a top portion extending transverse to the longitudinal centerline and having a top surface and a bottom surface,
a skirt having a top surface, downwardly depending from the top portion, and being configured to telescopically snap fit under a flange of the IV bottle crown,
the top portion having an internal chamber, the internal chamber extending between the bottom surface of the top portion and the top surface of the skirt in a plane transverse to the longitudinal centerline,
a cannula configured to puncture the IV bottle stopper for fluid communication with the IV bottle upon mounting on the IV bottle crown, the cannula having a tip portion with an opening, such that when the cannula is inserted into the IV bottle stopper, the tip portion is the only portion of the cannula exposed to the infusion liquid of the IV bottle, wherein the cannula includes a vent lumen, the top portion includes at least one vent through the top surface of the top portion, the at least one vent being in fluid communication with the internal chamber and the vent lumen,
an upright nipple on the top surface of the top portion oppositely directed with respect to the cannula, the upright nipple having a first nipple section with a first nipple section lumen in fluid communication with a cannula liquid lumen of the cannula, and the upright nipple having a second nipple section with a second nipple section lumen in fluid communication with the cannula liquid lumen, the first nipple section and the second nipple section being angularly offset from one another;
an IV port extending from the first nipple section and including a sealing membrane comprising a material puncturable by the IV spike of the infusion set, the IV port including a fixed portion having a first pair of opposing tabs and a removable portion having a second pair of opposing tabs, wherein the sealing membrane is at a junction of the fixed portion and the removeable portion, and the removable portion is configured to be twisted off the fixed portion to expose the sealing membrane without leading to flow communication beyond the sealing membrane; and
a needleless self-sealing port extending from the second nipple section, the needleless self-sealing port configured to couple with the male connector of the additive transfer device.

2. The liquid transfer device of claim 1, wherein the flange is configured to serve as a stop for the IV bottle crown.

3. The liquid transfer device of claim 1, wherein the upright nipple is Y-shaped.

4. The liquid transfer device of claim 1, wherein the male connector of the additive transfer device is a male Luer lock connector.

5. The liquid transfer device of claim 1, wherein the additive transfer device comprises a syringe containing a liquid medicament.

6. The liquid transfer device of claim 1, wherein the additive transfer device comprises a vial containing at least one of a liquid or solid medicament.

7. The liquid transfer device of claim 1, wherein a diameter of the flange of the IV bottle crown is greater than a diameter of the open IV bottle neck.

8. The liquid transfer device of claim 1, wherein the cannula has a length that is substantially similar to a height of the IV bottle stopper.

9. The liquid transfer device of claim 1, wherein the cannula has a length longer than a height of the IV bottle stopper.

10. The liquid transfer device of claim 1, wherein the cannula liquid lumen extends along the longitudinal centerline, and the vent lumen is offset from the cannula liquid lumen.

11. The liquid transfer device of claim 10, wherein the opening of the tip portion of the cannula opens to the cannula liquid lumen, and a second opening of the tip portion of the cannula opens to the vent lumen.

12. The liquid transfer device of claim 1, wherein the vial adapter has an air filter in the internal chamber.

13. A method of preparing a medication for intravenous administration of infusion liquid to a patient using a liquid transfer device, an intravenous (IV) bottle, an additive transfer device and an infusion set with an IV spike, the IV bottle including a closed end tapering towards an open IV bottle neck and containing an infusion liquid, and an IV bottle crown mounted on a collar around the IV bottle neck and having an IV bottle stopper for sealing the IV bottle, and the additive transfer device having a male connector, the method comprising:
coupling the male connector of the additive transfer device to a self-sealing port of the liquid transfer device;
telescopically snap fitting a skirt of a vial adapter of the liquid transfer device under a flange of the IV bottle crown and puncturing the IV bottle stopper with a cannula of the liquid transfer device, the cannula having a cannula liquid lumen and a tip portion with an opening, so that the tip portion is the only portion of the cannula exposed to the infusion liquid of the IV bottle;
mixing an additive contained in the additive transfer device with the infusion liquid;
venting the IV bottle through a vent lumen in the cannula, an internal chamber of a top portion, and at least one vent through a top surface of the top portion, the internal chamber extending between a bottom surface of the top portion and a top surface of the skirt in a plane transverse to a longitudinal centerline of the liquid transfer device;
twisting off a removable portion of an IV port of the liquid transfer device from a fixed portion of the IV port to expose a sealing membrane in the IV port at a junction of the fixed portion and the removeable portion without leading to flow communication beyond the sealing membrane; and
puncturing the sealing membrane of the liquid transfer device with the IV spike of the infusion set.

14. The method of claim 13, wherein the male connector of the additive transfer device is a male Luer lock connector.

15. The method of claim 13, wherein the additive transfer device comprises a syringe containing a liquid medicament.

16. The method of claim 13, wherein the additive transfer device comprises:
a vial containing at least one of a liquid or solid medicament; and
the vial adapter having the male connector.

17. The method of claim 13, wherein the flange is configured to serve as a stop for the IV bottle crown.

18. The method of claim 13, further comprising inverting the additive transfer device to drain its contents through the liquid transfer device while minimizing a dead space volume.

19. The method of claim 13, wherein the cannula liquid lumen extends along the longitudinal centerline, and the vent lumen is offset from the cannula liquid lumen.

20. The method of claim 19, wherein the opening of the tip portion of the cannula opens to the cannula liquid lumen and a second opening of the tip portion of the cannula opens to the vent lumen.

21. The method of claim 13, wherein venting the IV bottle is through an air filter in the internal chamber.

* * * * *